United States Patent [19]
Pieken et al.

[11] Patent Number: 5,958,691
[45] Date of Patent: *Sep. 28, 1999

[54] HIGH AFFINITY NUCLEIC ACID LIGANDS CONTAINING MODIFIED NUCLEOTIDES

[75] Inventors: Wolfgang Pieken, Longmont; Diane Tasset, Boulder; Nebojsa Janjic, Lafayette; Larry Gold, Boulder; Gary P. Kirschenheuter, Arvada, all of Colo.

[73] Assignee: NeXstar Pharmaceuticals, Inc., Boulder, Colo.

[*] Notice: This patent is subject to a terminal disclaimer.

[21] Appl. No.: 08/918,304

[22] Filed: Aug. 25, 1997

Related U.S. Application Data

[63] Continuation of application No. 08/430,709, Apr. 27, 1995, Pat. No. 5,660,985, which is a continuation of application No. 08/117,991, Sep. 8, 1993, abandoned, which is a continuation-in-part of application No. 07/714,131, Jun. 10, 1991, Pat. No. 5,475,096, and application No. 07/536,428, Jun. 11, 1990, abandoned, and application No. 07/973,333, Nov. 6, 1992, Pat. No. 5,476,766, and application No. 07/964,624, Oct. 21, 1992, Pat. No. 5,496,938.

[51] Int. Cl.$^6$ .............................. C12Q 1/68; C12P 19/34; C07H 21/02; C07H 21/04
[52] U.S. Cl. ........................ 435/6; 435/91.2; 536/24.31; 536/24.5; 536/23.1; 536/22.1; 935/77; 935/78
[58] Field of Search ..................... 435/6, 91.2; 536/24.5, 536/22.1, 23.1, 24.31; 935/77, 78

[56] References Cited

U.S. PATENT DOCUMENTS

| | | | |
|---|---|---|---|
| 5,270,163 | 12/1993 | Gold et al. | 435/6 |
| 5,475,096 | 12/1995 | Gold et al. | 536/23.1 |
| 5,476,766 | 12/1995 | Gold et al. | 435/6 |
| 5,543,293 | 8/1996 | Gold et al. | 435/6 |
| 5,660,985 | 8/1997 | Peiken et al. | 435/6 |

FOREIGN PATENT DOCUMENTS

| | | |
|---|---|---|
| B-47586/90 | 11/1989 | Australia . |
| 2 183 661 | 6/1987 | United Kingdom . |
| WO 89/06694 | 7/1989 | WIPO . |
| WO 92/14843 | 9/1992 | WIPO . |

OTHER PUBLICATIONS

Matthews and Kricka (1988) Analytical Biochemistry 169:1.

Joyce (1989) Gene 82:83.

Joyce & Inoue (1989) Nucleic Acids Research 17:711.

Ellington & Szostak (1990) Abstract of papers presented at the 1990 meeting on RNA Processing, Cold Spring Harbor Laboratory, Cold Spring Harbor, NY, p. 84.

Kinzler & Vogelstein (1989) Nucleic Acids Research 17:3645.

Kramer et al. (1974) J. Mol. Biol. 89:719.

Levisohn & Spiegelman (1969) Proc. Natl. Acad. Sci. USA 63:805.

Levisohn & Spiegelman (1968) Proc. Natl. Acad. Sci. USA 60:866.

Oliphant et al. (1989) Mol. Cell. Biol.9:2944.

Oliphant & Struhl (1988) Nucleic Acids Research 16:7673.

Oliphant & Struhl (1987) Methods in Enzymology 155:568.

Oliphant et al. (1986) Gene 44:177.

Robertson & Joyce (1990) Nature 344:467.

Thiesen & Bach (1990) Nucleic Acids Research 18:3203.

*Primary Examiner*—Stephanie W. Zitomer
*Attorney, Agent, or Firm*—Swanson & Bratschun LLC

[57] ABSTRACT

Nucleic acid ligands containing modified nucleotides are described as are methods for producing such oligonucleotides. Such ligands enrich the chemical diversity of the candidate mixture for the SELEX process. Specific examples are provided of nucleic acids containing nucleotides modified at the 2'- and 5-position. Specific 2-OH and 2'-NH$_2$ modified RNA ligands to thrombin are described.

24 Claims, 20 Drawing Sheets

| Side Chain | Structure | Target: | Reference |
|---|---|---|---|
| MQPA | 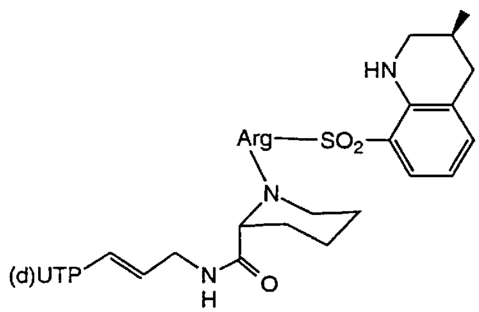 | Thrombin | Kikumoto et al. (1984) *Biochemistry* 23, 85. |
| RGD | 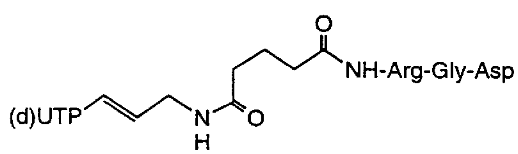 | Integrins (GP IIb/IIIa) | Rouslahti et al. (1986) *Cell* 44, 517. |
| Y | 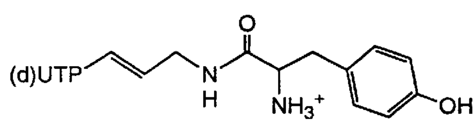 | Tyrosine Kinases | Bolen (1993) *Oncogene* 8, 2025. |

THROMBIN 2'OH RNA BINDING SEQUENCES--ROUND 12
Class I
(22 clones)

| | 5' fixed | 30N variable | 3' fixed | SEQ ID NO: |
|---|---|---|---|---|
| #1 | GGGAGAUGCCUGUCGAGCAUGCUG | AGGAUCGAAGUUAGUAGGCUUUGUGUGCUC | GUAGCUAAACAGCUUUGUCGACUCU | 1 |
| #6 | GGGAGAUGCCUGUCGAGCAUGCUG | AGGAUCGAAGUUAGUAGGCUUUGUGUGCUC | GUAGCUAAACAGCUUUGUCGACUCU | 1 |
| #13 | GGGAGAUGCCUGUCGAGCAUGCUG | AGGAUCGAAGUUAGUAGGCUUUGUGUGCUC | GUAGCUAAACAGCUUUGUCGACUCU | 1 |
| #19 | GGGAGAUGCCUGUCGAGCAUGCUG | AGGAUCGAAGUUAGUAGGCUUUGUGUGCUC | GUAGCUAAACAGCUUUGUCGACUCU | 1 |
| #23 | GGGAGAUGCCUGUCGAGCAUGCUG | AGGAUCGAAGUUAGUAGGCUUUGUGUGCUC | GUAGCUAAACAGCUUUGUCGACUCU | 1 |
| #24 | GGGAGAUGCCUGUCGAGCAUGCUG | AGGAUCGAAGUUAGUAGGCUUUGUGUGCUC | GUAGCUAAACAGCUUUGUCGACUCU | 1 |
| #25 | GGGAGAUGCCUGUCGAGCAUGCUG | AGGAUCGAAGUUAGUAGGCUUUGUGUGCUC | GUAGCUAAACAGCUUUGUCGACUCU | 1 |
| #30 | GGGAGAUGCCUGUCGAGCAUGCUG | AGGAUCGAAGUUAGUAGGCUUUGUGUGCUC | GUAGCUAAACAGCUUUGUCGACUCU | 1 |
| #2 | GGGAGAUGCCUGUCGAGCAUGCUG | UACUGGAUCGAAGGUAGUAGGCAGUCAC | GUAGCUAAACAGCUUUGUCGACUCU | 2 |
| #5 | GGGAGAUGCCUGUCGAGCAUGCUG | AUAUCACGGAUCGAAGGAAGUAGGCGUG | GUAGCUAAACAGCUUUGUCGACUCU | 3 |
| #9 | GGGAGAUGCCUGUCGAGCAUGCUG | CCUUUCCCGGUUCGAAGUCAGUAGGCCGG | GUAGCUAAACAGCUUUGUCGACUCU | 4 |
| #10 | GGGAGAUGCCUGUCGAGCAUGCUG | CACCCGGAUCGAAGUUAGUAGGCGUGAGU | GUAGCUAAACAGCUUUGUCGACUCU | 5 |
| #15 | GGGAGAUGCCUGUCGAGCAUGCUG | UGUACGGAUCGAAGGUAGUAGGCAGGUUAC | GUAGCUAAACAGCUUUGUCGACUCU | 6 |
| #16 | GGGAGAUGCCUGUCGAGCAUGCUG | CAUCCGGAUCGAAGUUAGUAGGCGGAGUG | GUAGCUAAACAGCUUUGUCGACUCU | 7 |
| #18 | GGGAGAUGCCUGUCGAGCAUGCUG | AUUGUUGCGGAUCGAAGUGGAGUAGGCGCA | GUAGCUAAACAGCUUUGUCGACUCU | 8 |

FIGURE 6A-1

| | 5' fixed | 30N variable | 3' fixed | SEQ ID NO: |
|---|---|---|---|---|
| #21 | GGGAGAUGCCUGUCGAGCAUGCUG | UGUACUGGAUCGAAGGUAGUAGGCAGUCAC | GUAGCUAAACAGCUUUGUCGACUCU | 9 |
| #22 | GGGAGAUGCCUGUCGAGCAUGCUG | AUCGAAGUUAGUAGGAGCCGUGUG | GUAGCUAAACAGCUUUGUCGACUCU | 10 |
| #26 | GGGAGAUGCCUGUCGAGCAUGCUG | ACGCUGGAGAGUCGGAUCGAAAGGUAAGUAGGCGACU | GUAGCUAAACAGCUUUGUCGACUCU | 11 |
| #31 | GGGAGAUGCCUGUCGAGCAUGCUG | GGGUCGGAUCGAAAGGUAAGUAGGCGACU | GUAGCUAAACAGCUUUGUCGACUCU | 12 |
| #33 | GGGAGAUGCCUGUCGAGCAUGCUG | AUAUCACGGAUCGAAAGAGAGUAGGCGU | GUAGCUAAACAGCUUUGUCGACUCU | 13 |
| #34 | GGGAGAUGCCUGUCGAGCAUGCUG | UGUACUGGAUCGAAGGUAGUAGGCAGGCAC | GUAGCUAAACAGCUUUGUCGACUCU | 14 |
| #37 | GGGAGAUGCCUGUCGAGCAUGCUG | AUAUCACGGAUCGAAGGAAAGUAGGCGUG | GUAGCUAAACAGCUUUGUCGACUCU | 15 |

Class II
(6 clones)

| | 5' fixed | 30N variable | 3' fixed | |
|---|---|---|---|---|
| #3 | GGGAGAUGCCUGUCGAGCAUGCUG | GUGCGGCCUUUGGGCGCCGUGCUUGGC | GUAGCUAAACAGCUUUGUCGACUCU | 16 |
| #20 | GGGAGAUGCCUGUCGAGCAUGCUG | GUGCGGCCUUUGGGCGCCGUGCUUAC | GUAGCUAAACAGCUUUGUCGACUCU | 17 |
| #27 | GGGAGAUGCCUGUCGAGCAUGCUG | GUGCGGCCUUUGGGCGCCGUGCUUGAC | GUAGCUAAACAGCUUUGUCGACUCU | 18 |
| #35 | GGGAGAUGCCUGUCGAGCAUGCUG | GGGCGGCCUUUGGGCGCCGUGCUUGAC | GUAGCUAAACAGCUUUGUCGACUC | 19 |
| #38 | GGGAGAUGCCUGUCGAGCAUGCUG | GUGCGGCCUUUGGGCGCCGUGCUUGAC | GUAGCUAAACAGCUUUGUCGACUCU | 18 |
| #39 | GGGAGAUGCCUGUCGAGCAUGCUG | GUGCGGCCUUUGGGCGCCGUGCUUGAC | GUAGCUAAACAGCUUUGUCGACUCU | 18 |

FIGURE 6A-2

THROMBIN 2'NH₂ RNA SEQUENCES--ROUND 15

Group I (15 clones)

| | 5' fixed | 30N variable | 3' fixed | SEQ ID NO: |
|---|---|---|---|---|
| #32 | GGGAGAUGCCUGUCGAGCAUGCUG | UGAGCCUGCCAGUGUAUGUGAAACAAG | GUAGCUAAACAGCUUUGUCGACUCU | 20 |
| #2 | GGGAGAUGCCUGUCGAGCAUGCUG | UGAGCCUGCCAGUGCAUGUGAAACAAG | GUAGCUAAACAGCUUUGUCGACUCU | 21 |
| #12, 27 | GGGAGAUGCCUGUCGAGCAUGCUG | UGAGCCAGCCAGUGUGCAUGUGAAACAAG | GUAGCUAAACAGCUUUGUCGACUCU | 22 |
| #30, 31, 35, 39, 48 #13, 20 | GGGAGAUGCCCUGUCGAGCAUGCUG | UGAGCCAGCCAGUGUAUGUGAAACAAG | GUAGCUAAACAGCUUUGUCGACUCU | 23 |
| #28, 42 #23 | GGGAGAUGCCUGUCGAGCAUGCUG | UGAGCCGGCCAGUGUGCAUGUGAAACAAG | GUAGCUAAACAGCUUUGUCGACUCU | 24 |
| #46 | GGGAGAUGCCUGUCGAGCAUGCUG | UGAGCCAGCCAGUGCGUAUGUGAAACAAG | GUAGCUAAACAGCUUUGUCGACUCU | 25 |

FIGURE 6B-1

Group II  (30 clones)
Group IIA (25 clones)

| | 5' fixed | 30N variable | 3' fixed | SEQ ID NO: |
|---|---|---|---|---|
| #33,43 | GGGAGAUGCCUGUCGAGCAUGCUG | UUACGGGGAGGUGUUAGGGAGUGUACCC | GUAGCUAAACAGCUUUGUCGACUCU | 26 |
| #3,14 | GGGAGAUGCCUGUCGAGCAUGCUG | UUGCGGG(A)GAGGUGUUAGGGAGUGUACCC | GUAGCUAAACAGCUUUGUCGACUCU | 27 |
| #8,15,34,38,40,51 #6 | GGGAGAUGCCUGUCGAGCAUGCUG | UUGCGGGGAGGUGUUAGXXAGUGUACCC | GUAGCUAAACAGCUUUGUCGACUCU | 28 |
| #24 | GGGAGAUGCCUGUCGAGCAUGCUG | UUGCGGG(A)GAGGUGUUAGGGAGUCACCC | GUAGCUAAACAGCUUUGUCGACUCU | 29 |
| #7,9 | GGGAGAUGCCUGUCGAGCAUGCUG | CUGCGGGGAGGUGUUAGGGAGUGUACCC | GUAGCUAAACAGCUUUGUCGACUCU | 30 |
| #26,36,37,41,52,54 #10,18 | GGGAGAUGCCUGUCGAGCAUGCUG | CUGCGGGGAGGUGUUAGAGAGUGUACCC | GUAGCUAAACAGCUUUGUCGACUCU | 31 |
| #11 | GGGAGAUGCCUGUCGAGCAUGCUG | CUGCGGGGAGGUGUCAGAGAGUGUACCC | GUAGCUAAACAGCUUUGUCGACUCU | 32 |
| #22 | GGGAGAUGCCUGUCGAGCAUGCUG | CUACGGGGAGGUGUUAGAGAGUGUACCC | GUAGCUAAACAGCUUUGUCGACUCU | 33 |
| #53 | GGGAGAUGCCUGUCGAGCAUGCUG | CUACGGGGAGGUGUCGGAGAGUGUACCU | GUAGCUAAACAGCUUUGUCGACUCU | 34 |

Group IIB (5 clones)

| | 5' fixed | 30N variable | 3' fixed | SEQ ID NO: |
|---|---|---|---|---|
| #4 | GGGAGAUGCCUGUCGAGCAUGCUG | CACGAGGUGUCAGAGAGUGUA(G)GUUCAGC | GUAGCUAAACAGCUUUGUCGACUCU | 35 |
| #17,50 | GGGAGAUGCCUGUCGAGCAUGCUG | CACGAGGUGUCAGAGAGUGUAGUGCAGC | GUAGCUAAACAGCUUUGUCGACUCU | 36 |
| #1 | GGGAGAUGCCUGUCGAGCAUGCUG | CACGAGGUGUAGAGGGUGUAGUGCAGCA | GUAGCUAAACAGCUUUGUCGACUCU | 37 |
| #5 | GGGAGAUGCCUGUCGAGCAUGCUG | CACGAGGCGUCAGAGAGUGUA(U)GUGCUGC | GUAGCUAAACAGCUUUGUCGACUCU | 38 |

FIGURE 6B-2

Group III (2 clones)

SEQ ID NO: 39

5' fixed | 30N variable | 3' fixed

29 GGGAGAUGCCUGUCGAGCAUGCUG AGGAUCGAAGUAGUAGGCUUUGUGCUC GUAGCUAAACAGCUUGUCGACUCU

FIGURE 6B-3

```
            G   G
        AGUU A   U
       A          A
      G            G
      C   A      G
       U    G - C
            C - G
            C - G
            U - A
            A - G
            C   U
            g   g
            g - u
            u - a
            c - g
            g - c
```

5'-gggagaugccugucgagcau    uaaacagcuuugucgacggg-3' kD = 30nM

CLASS 1  
Clone 16  
SEQ ID NO:7

FIGURE 7A

```
                      G  U
                    U      G
                   A  10    G
                    U      A
                     G   A
                      U-A
                      G-C
                      U-A
                      G  A
                      A
                      C-G
                      C-g
                      G-u
                      U-a
                      C
kD = 400nM            C-g
                      G-c
                      A-u
                         a
                      G  a
                      U-a
                      g-c
                      u-a
                      c-g
                      g-c
                         u
                    u    u
                     a-u
                     c-g
5'-gggagaugccugucgag    ucgacggg-3'
```

GROUP I
Clone 32
SEQ ID NO:20

FIGURE 7C

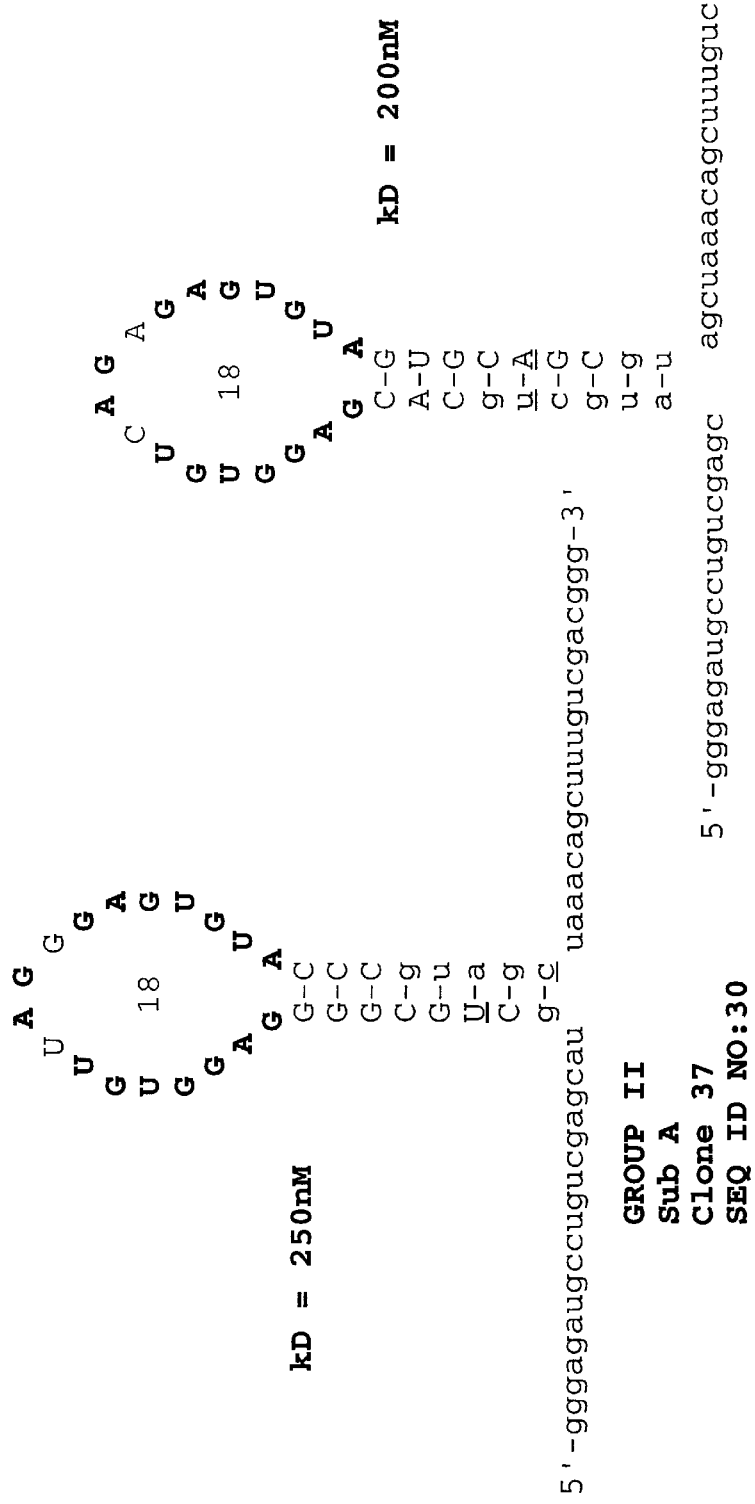

```
        G  U
      A 4 A
      U - G
      U - G
      G - C
      A - U
      A - U
        G - U
        C - G
            U
        U - G
        A - U
       G   G
        G - C
        A - U
        g - C
          u - g   uagcuaaacagcuuugucgacggg-3'
5'-gggagaugccugucgagcaugc kD_OH = 100nM GROUP III
Clone 29
SEQ ID NO:39 acgu = fixed region
ACGU = random region
ACGU = conserved region
```

FIGURE 7F

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
       (A) LENGTH: 79 base pairs
       (B) TYPE: nucleic acid
       (C) STRANDEDNESS: single
       (D) TOPOLOGY:    linear (xi) SEQUENCE DESCRIPTION: SEQ ID NO:1:

```
GGGAGAUGCC UGUCGAGCAU GCUGAGGAUC GAAGUUAGUA GGCUUUGUGU          50

GCUCGUAGCU AAACAGCUUU GUCGACUCU                                  79
```

(2) INFORMATION FOR SEQ ID NO:2:

(i) SEQUENCE CHARACTERISTICS:
       (A) LENGTH: 76 base pairs
       (B) TYPE: nucleic acid
       (C) STRANDEDNESS: single
       (D) TOPOLOGY:    linear (xi) SEQUENCE DESCRIPTION: SEQ ID NO:2:

```
GGGAGAUGCC UGUCGAGCAU GCUGUACUGG AUCGAAGGUA GUAGGCAGUC          50

ACGUAGCUAA ACAGCUUUGU GACUCU                                     76
```

(2) INFORMATION FOR SEQ ID NO:3:

(i) SEQUENCE CHARACTERISTICS:
       (A) LENGTH: 76 base pairs
       (B) TYPE: nucleic acid
       (C) STRANDEDNESS: single
       (D) TOPOLOGY:    linear (xi) SEQUENCE DESCRIPTION: SEQ ID NO:3:

```
GGGAGAUGCC UGUCGAGCAU GCUGAUAUCA CGGAUCGAAG GAAGUAGGCG          50

UGGUAGCUAA ACAGCUUUGU GACUCU                                     76
```

(2) INFORMATION FOR SEQ ID NO:4:

(i) SEQUENCE CHARACTERISTICS:
       (A) LENGTH: 79 base pairs
       (B) TYPE: nucleic acid
       (C) STRANDEDNESS: single
       (D) TOPOLOGY:    linear (xi) SEQUENCE DESCRIPTION: SEQ ID NO:4:

```
GGGAGAUGCC UGUCGAGCAU GCUGCCUUUC CCGGGUUCGA AGUCAGUAGG          50

CCGGGUAGCU AAACAGCUUU GUCGACUCU                                  79
```

(2) INFORMATION FOR SEQ ID NO:5:

(i) SEQUENCE CHARACTERISTICS:
       (A) LENGTH: 78 base pairs
       (B) TYPE: nucleic acid
       (C) STRANDEDNESS: single
       (D) TOPOLOGY:    linear (xi) SEQUENCE DESCRIPTION: SEQ ID NO:5:

```
GGGAGAUGCC UGUCGAGCAU GCUGCACCCG GAUCGAAGUU AGUAGGCGUG          50
```

```
AGUGUAGCUA AACAGCUUUG UCGACUCU                                                78

(2) INFORMATION FOR SEQ ID NO:6:

(i) SEQUENCE CHARACTERISTICS:
         (A) LENGTH: 79 base pairs
         (B) TYPE: nucleic acid
         (C) STRANDEDNESS: single
         (D) TOPOLOGY:    linear (xi) SEQUENCE DESCRIPTION: SEQ ID NO:6:

GGGAGAUGCC UGUCGAGCAU GCUGUGUACG GAUCGAAGGU AGUAGGCAGG                         50

UUACGUAGCU AAACAGCUUU GUCGACUCU                                               79

(2) INFORMATION FOR SEQ ID NO:7:

(i) SEQUENCE CHARACTERISTICS:
         (A) LENGTH: 77 base pairs
         (B) TYPE: nucleic acid
         (C) STRANDEDNESS: single
         (D) TOPOLOGY:    linear (xi) SEQUENCE DESCRIPTION: SEQ ID NO:7:

GGGAGAUGCC UGUCGAGCAU GCUGCAUCCG GAUCGAAGUU AGUAGGCGGA                         50

GUGGUAGCUA AACAGCUUUG CGACUCU                                                 77

(2) INFORMATION FOR SEQ ID NO:8:

(i) SEQUENCE CHARACTERISTICS:
         (A) LENGTH: 79 base pairs
         (B) TYPE: nucleic acid
         (C) STRANDEDNESS: single
         (D) TOPOLOGY:    linear (xi) SEQUENCE DESCRIPTION: SEQ ID NO:8:

GGGAGAUGCC UGUCGAGCAU GCUGAUUGUU GCGGAUCGAA GUGGAGUAGG                         50

CGCAGUAGCU AAACAGCUUU GUCGACUCU                                               79

(2) INFORMATION FOR SEQ ID NO:9:

(i) SEQUENCE CHARACTERISTICS:
         (A) LENGTH: 79 base pairs
         (B) TYPE: nucleic acid
         (C) STRANDEDNESS: single
         (D) TOPOLOGY:    linear (xi) SEQUENCE DESCRIPTION: SEQ ID NO:9:

GGGAGAUGCC UGUCGAGCAU GCUGUGUACU GGAUCGAAGG UAGUAGCGAG                         50

UCACGUAGCU AAACAGCUUU GUCGACUCU                                               79

(2) INFORMATION FOR SEQ ID NO:10:

(i) SEQUENCE CHARACTERISTICS:
         (A) LENGTH: 72 base pairs
         (B) TYPE: nucleic acid
         (C) STRANDEDNESS: single
         (D) TOPOLOGY:    linear (xi) SEQUENCE DESCRIPTION: SEQ ID NO:10:

GGGAGAUGCC UGUCGAGCAU GCUGAUCGAA GUUAGUAGGA GCGUGUGGUA                         50

GCUAAACAGC UUUGUCGACU CU                                                      72

(2) INFORMATION FOR SEQ ID NO:11:
```

(i) SEQUENCE CHARACTERISTICS:
        (A) LENGTH: 84 base pairs
        (B) TYPE: nucleic acid
        (C) STRANDEDNESS: single
        (D) TOPOLOGY:    linear (xi) SEQUENCE DESCRIPTION: SEQ ID NO:11:

GGGAGAUGCC UGUCGAGCAU GCUGACGCUA GAGUCGGAUC GAAAGGUAAG          50

UAGGCGACUG UAGCUAAACA GCUUUGUCGA CUCU                          84

(2) INFORMATION FOR SEQ ID NO:12:

(i) SEQUENCE CHARACTERISTICS:
        (A) LENGTH: 79 base pairs
        (B) TYPE: nucleic acid
        (C) STRANDEDNESS: single
        (D) TOPOLOGY:    linear (xi) SEQUENCE DESCRIPTION: SEQ ID NO:12:

GGGAGAUGCC UGUCGAGCAU GCUGGGGUCG GAUCGAAAGG UAAGUAGGCG          50

ACUGUAGCUA AACAGCUCUU GUCGACUCU                                79

(2) INFORMATION FOR SEQ ID NO:13:

(i) SEQUENCE CHARACTERISTICS:
        (A) LENGTH: 77 base pairs
        (B) TYPE: nucleic acid
        (C) STRANDEDNESS: single
        (D) TOPOLOGY:    linear (xi) SEQUENCE DESCRIPTION: SEQ ID NO:13:

GGGAGAUGCC UGUCGAGCAU GCUGAUAUCA CGGAUCGAAA GAGAGUAGGC          50

GUGUAGCUAA ACAGCUUUGU CGACUCU                                  77

(2) INFORMATION FOR SEQ ID NO:14:

(i) SEQUENCE CHARACTERISTICS:
        (A) LENGTH: 79 base pairs
        (B) TYPE: nucleic acid
        (C) STRANDEDNESS: single
        (D) TOPOLOGY:    linear (xi) SEQUENCE DESCRIPTION: SEQ ID NO:14:

GGGAGAUGCC UGUCGAGCAU GCUGUGUACU GGAUCGAAGG UAGUAGGCAG          50

GCACGUAGCU AAACAGCUUU GUCGACUCU                                79

(2) INFORMATION FOR SEQ ID NO:15:

(i) SEQUENCE CHARACTERISTICS:
        (A) LENGTH: 78 base pairs
        (B) TYPE: nucleic acid
        (C) STRANDEDNESS: single
        (D) TOPOLOGY:    linear (xi) SEQUENCE DESCRIPTION: SEQ ID NO:15:

GGGAGAUGCC UGUCGAGCAU GCUGAUAUCA CGGAUCGAAG GAAAGUAGGC          50

GUGGUAGCUA AACAGCUUUG UCGACUCU                                 78

(2) INFORMATION FOR SEQ ID NO:16:

(i) SEQUENCE CHARACTERISTICS:
        (A) LENGTH: 75 base pairs
        (B) TYPE: nucleic acid
        (C) STRANDEDNESS: single
        (D) TOPOLOGY:    linear (xi) SEQUENCE DESCRIPTION: SEQ ID NO:16:

GGGAGAUGCC UGUCGAGCAU GCUGGUGCGG CUUUGGGCGC CGUGCUUGGC      50

GUAGCUAAAC AGCUUUGUCG ACUCU                                 75

(2) INFORMATION FOR SEQ ID NO:17:

(i) SEQUENCE CHARACTERISTICS:
        (A) LENGTH: 74 base pairs
        (B) TYPE: nucleic acid
        (C) STRANDEDNESS: single
        (D) TOPOLOGY:   linear (xi) SEQUENCE DESCRIPTION: SEQ ID NO:17:

GGGAGAUGCC UGUCGAGCAU GCUGGUGCGG CUUUGGGCGC CGUGCUUACG      50

UAGCUAAACA GCUUUGUCGA CUCU                                  74

(2) INFORMATION FOR SEQ ID NO:18:

(i) SEQUENCE CHARACTERISTICS:
        (A) LENGTH: 75 base pairs
        (B) TYPE: nucleic acid
        (C) STRANDEDNESS: single
        (D) TOPOLOGY:   linear (xi) SEQUENCE DESCRIPTION: SEQ ID NO:18:

GGGAGAUGCC UGUCGAGCAU GCUGGUGCGG CUUUGGGCGC CGUGCUUGAC      50

GUAGCUAAAC AGCUUUGUCG ACUCU                                 75

(2) INFORMATION FOR SEQ ID NO:19:

(i) SEQUENCE CHARACTERISTICS:
        (A) LENGTH: 74 base pairs
        (B) TYPE: nucleic acid
        (C) STRANDEDNESS: single
        (D) TOPOLOGY:   linear (xi) SEQUENCE DESCRIPTION: SEQ ID NO:19:

GGGAGAUGCC UGUCGAGCAU GCUGGGGCGG CUUUGGGCGC CGUGCUUGAC      50

GUAGCUAAAC AGCUUUGUCG ACUC                                  74

(2) INFORMATION FOR SEQ ID NO:20:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ix) FEATURE:  All pyrimidines are 2'-NH2 modified (xi) SEQUENCE DESCRIPTION: SEQ ID NO:20:

GGGAGAUGCC UGUCGAGCAU GCUGUGAGCC UGCCAGUGUG UAUGUGGAAA      50

CAAGGUAGCU AAACAGCUUU GUCGACUCU                             79

(2) INFORMATION FOR SEQ ID NO:21:

(i) SEQUENCE CHARACTERISTICS:
        (A) LENGTH: 79 base pairs
        (B) TYPE: nucleic acid
        (C) STRANDEDNESS: single
        (D) TOPOLOGY:   linear (ix) FEATURE:  All pyrimidines are 2'-NH2 modified (xi) SEQUENCE DESCRIPTION: SEQ ID NO:21:

GGGAGAUGCC UGUCGAGCAU GCUGUGAGCC UGCCAGUGUG CAUGUGGAAA         50

CAAGGUAGCU AAACAGCUUU GUCGACUCU                                79

(2) INFORMATION FOR SEQ ID NO:22:

(i) SEQUENCE CHARACTERISTICS:
        (A) LENGTH: 79 base pairs
        (B) TYPE: nucleic acid
        (C) STRANDEDNESS: single
        (D) TOPOLOGY:    linear (ix) FEATURE:  All pyrimidines are 2'-NH2 modified (xi) SEQUENCE DESCRIPTION: SEQ ID NO:22:

GGGAGAUGCC UGUCGAGCAU GCUGUGAGCC AGCCAGUGUG CAUGUGGAAA         50

CAAGGUAGCU AAACAGCUUU GUCGACUCU                                79

(2) INFORMATION FOR SEQ ID NO:23:

(i) SEQUENCE CHARACTERISTICS:
        (A) LENGTH: 79 base pairs
        (B) TYPE: nucleic acid
        (C) STRANDEDNESS: single
        (D) TOPOLOGY:    linear (ix) FEATURE:  All pyrimidines are 2'-NH2 modified (xi) SEQUENCE DESCRIPTION: SEQ ID NO:23:

GGGAGAUGCC UGUCGAGCAU GCUGUGAGCC AGCCAGUGUG UAUGUGGAAA         50

CAAGGUAGCU AAACAGCUUU GUCGACUCU                                79

(2) INFORMATION FOR SEQ ID NO:24:

(i) SEQUENCE CHARACTERISTICS:
        (A) LENGTH: 79 base pairs
        (B) TYPE: nucleic acid
        (C) STRANDEDNESS: single
        (D) TOPOLOGY:    linear (ix) FEATURE:  All pyrimidines are 2'-NH2 modified (xi) SEQUENCE DESCRIPTION: SEQ ID NO:24:

GGGAGAUGCC UGUCGAGCAU GCUGUGAGCC GGCCAGUGUG CAUGUGGAAA         50

CAAGGUAGCU AAACAGCUUU GUCGACUCU                                79

(2) INFORMATION FOR SEQ ID NO:25:

(i) SEQUENCE CHARACTERISTICS:
        (A) LENGTH: 79 base pairs
        (B) TYPE: nucleic acid
        (C) STRANDEDNESS: single
        (D) TOPOLOGY:    linear (ix) FEATURE:  All pyrimidines are 2'-NH2 modified (xi) SEQUENCE DESCRIPTION: SEQ ID NO:25:

GGGAGAUGCC UGUCGAGCAU GCUGUGAGCC AGCCAGUGUG UAUGUGGAAA         50

CAAGGUAGCU AAACAGCUUU GUCGACUCU                                79

(2) INFORMATION FOR SEQ ID NO:26:

(i) SEQUENCE CHARACTERISTICS:
        (A) LENGTH: 77 base pairs
        (B) TYPE: nucleic acid (C) STRANDEDNESS: single
        (D) TOPOLOGY:     linear (ix) FEATURE: All pyrimidines are 2'-NH2 modified (xi) SEQUENCE DESCRIPTION: SEQ ID NO:26:

GGGAGAUGCC UGUCGAGCAU GCUGUUACGG GGAGGUGUUA CGGAGUGUAC          50

CCGUAGCUAA ACAGCUUUGU CGACUCU                                  77

(2) INFORMATION FOR SEQ ID NO:27:

(i) SEQUENCE CHARACTERISTICS:
        (A) LENGTH: 77 base pairs
        (B) TYPE: nucleic acid
        (C) STRANDEDNESS: single
        (D) TOPOLOGY:     linear (ix) FEATURE: All pyrimidines are 2'-NH2 modified (xi) SEQUENCE DESCRIPTION: SEQ ID NO:27:

GGGAGAUGCC UGUCGAGCAU GCUGUUGCGG GGAGGUGUUA GGGAGUGUAC          50

CCGUAGCUAA ACAGCUUUGU CGACUCU                                  77

(2) INFORMATION FOR SEQ ID NO:28:

(i) SEQUENCE CHARACTERISTICS:
        (A) LENGTH: 77 base pairs
        (B) TYPE: nucleic acid
        (C) STRANDEDNESS: single
        (D) TOPOLOGY:     linear (ix) FEATURE: All pyrimidines are 2'-NH2 modified (xi) SEQUENCE DESCRIPTION: SEQ ID NO:28:

GGGAGAUGCC UGUCGAGCAU GCUGUUGCGG GGAGGUGUUA GNNAGUGUAC          50

CCGUAGCUAA ACAGCUUUGU CGACUCU                                  77

(2) INFORMATION FOR SEQ ID NO:29:

(i) SEQUENCE CHARACTERISTICS:
        (A) LENGTH: 77 base pairs
        (B) TYPE: nucleic acid
        (C) STRANDEDNESS: single
        (D) TOPOLOGY:     linear (ix) FEATURE: All pyrimidines are 2'-NH2 modified (xi) SEQUENCE DESCRIPTION: SEQ ID NO:29:

GGGAGAUGCC UGUCGAGCAU GCUGUUGCGG GGAGGUGUUA GGGAGUUCAC          50

CCGUAGCUAA ACAGCUUUGU CGACUCU                                  77

(2) INFORMATION FOR SEQ ID NO:30:

(i) SEQUENCE CHARACTERISTICS:
        (A) LENGTH: 77 base pairs
        (B) TYPE: nucleic acid
        (C) STRANDEDNESS: single
        (D) TOPOLOGY:     linear (ix) FEATURE: All pyrimidines are 2'-NH2 modified (xi) SEQUENCE DESCRIPTION: SEQ ID NO:30:

GGGAGAUGCC UGUCGAGCAU GCUGCUGCGG GGAGGUGUUA GGGAGUGUAC          50

CCGUAGCUAA ACAGCUUUGU CGACUCU                                  77

(2) INFORMATION FOR SEQ ID NO:31:

(i) SEQUENCE CHARACTERISTICS:
        (A) LENGTH: 77 base pairs
        (B) TYPE: nucleic acid
        (C) STRANDEDNESS: single
        (D) TOPOLOGY:    linear (ix) FEATURE: All pyrimidines are 2'-NH2 modified (xi) SEQUENCE DESCRIPTION: SEQ ID NO:31:

GGGAGAUGCC UGUCGAGCAU GCUGCUGCGG GGAGGUGUUA GAGAGUGUAC          50

CCGUAGCUAA ACAGCUUUGU CGACUCU                                  77

(2) INFORMATION FOR SEQ ID NO:32:

(i) SEQUENCE CHARACTERISTICS:
        (A) LENGTH: 77 base pairs
        (B) TYPE: nucleic acid
        (C) STRANDEDNESS: single
        (D) TOPOLOGY:    linear (ix) FEATURE: All pyrimidines are 2'-NH2 modified (xi) SEQUENCE DESCRIPTION: SEQ ID NO:32:

GGGAGAUGCC UGUCGAGCAU GCUGCUGCGG GGAGGUGUCA GAGAGUGUAC          50

CUGUAGCUAA ACAGCUUUGU CGACUCU                                  77

(2) INFORMATION FOR SEQ ID NO:33:

(i) SEQUENCE CHARACTERISTICS:
        (A) LENGTH: 77 base pairs
        (B) TYPE: nucleic acid
        (C) STRANDEDNESS: single
        (D) TOPOLOGY:    linear (ix) FEATURE: All pyrimidines are 2'-NH2 modified (xi) SEQUENCE DESCRIPTION: SEQ ID NO:33:

GGGAGAUGCC UGUCGAGCAU GCUGCUACGG GGAGGUGUUA GAGAGUGUAC          50

CUGUAGCUAA ACAGCUUUGU CGACUCU                                  77

(2) INFORMATION FOR SEQ ID NO:34:

(i) SEQUENCE CHARACTERISTICS:
        (A) LENGTH: 77 base pairs
        (B) TYPE: nucleic acid
        (C) STRANDEDNESS: single
        (D) TOPOLOGY:    linear (ix) FEATURE: All pyrimidines are 2'-NH2 modified (xi) SEQUENCE DESCRIPTION: SEQ ID NO:34:

GGGAGAUGCC UGUCGAGCAU GCUGCUACGG GGAGGUGUCG GAGAGUGUAC          50

CUGUAGCUAA ACAGCUUUGU CGACUCU                                  77

(2) INFORMATION FOR SEQ ID NO:35:

(i) SEQUENCE CHARACTERISTICS:
        (A) LENGTH: 77 base pairs
        (B) TYPE: nucleic acid
        (C) STRANDEDNESS: single
        (D) TOPOLOGY:    linear (ix) FEATURE: All pyrimidines are 2'-NH2 modified (xi) SEQUENCE DESCRIPTION: SEQ ID NO:35:

-continued

```
GGGAGAUGCC UGUCGAGCAU GCUGCACGAG GUGUCAGAGA GUGUAGUUCA                    50

GCGUAGCUAA ACAGCUUUGU CGACUCU                                             77
```

(2) INFORMATION FOR SEQ ID NO:36:

(i) SEQUENCE CHARACTERISTICS:
        (A) LENGTH: 77 base pairs
        (B) TYPE: nucleic acid
        (C) STRANDEDNESS: single
        (D) TOPOLOGY:   linear (ix) FEATURE:  All pyrimidines are 2'-NH2 modified (xi) SEQUENCE DESCRIPTION: SEQ ID NO:36:

```
GGGAGAUGCC UGUCGAGCAU GCUGCACGAG GUGUCAGAGA GUGUAGUGCA                    50

GCGUAGCUAA ACAGCUUUGU CGACUCU                                             77
```

(2) INFORMATION FOR SEQ ID NO:37:

(i) SEQUENCE CHARACTERISTICS:
        (A) LENGTH: 77 base pairs
        (B) TYPE: nucleic acid
        (C) STRANDEDNESS: single
        (D) TOPOLOGY:   linear (ix) FEATURE:  All pyrimidines are 2'-NH2 modified (xi) SEQUENCE DESCRIPTION: SEQ ID NO:37:

```
GGGAGAUGCC UGUCGAGCAU GCUGCACGAG GUGUAGAGGG UGUAGUGCAG                    50

CAGUACGUAA ACAGCUUUGU CGACUCU                                             77
```

(2) INFORMATION FOR SEQ ID NO:38:

(i) SEQUENCE CHARACTERISTICS:
        (A) LENGTH: 77 base pairs
        (B) TYPE: nucleic acid
        (C) STRANDEDNESS: single
        (D) TOPOLOGY:   linear (ix) FEATURE:  All pyrimidines are 2'-NH2 modified (xi) SEQUENCE DESCRIPTION: SEQ ID NO:38:

```
GGGAGAUGCC UGUCGAGCAU GCUGCACGAG GCGUCAGAGA GUGUAGUGCU                    50

GCGUACGUAA ACAGCUUUGU CGACUCU                                             77
```

(2) INFORMATION FOR SEQ ID NO:39:

(i) SEQUENCE CHARACTERISTICS:
        (A) LENGTH: 79 base pairs
        (B) TYPE: nucleic acid
        (C) STRANDEDNESS: single
        (D) TOPOLOGY:   linear (ix) FEATURE:  All pyrimidines are 2'-NH2 modified (xi) SEQUENCE DESCRIPTION: SEQ ID NO:39:

```
GGGAGAUGCC UGUCGAGCAU GCUGAGGAUC GAAGUUAGUA GGCUUUGUGU                    50

ACUCGUAGCU AAACAGCUUU GUCCACUCU                                           79
```

HIGH AFFINITY NUCLEIC ACID LIGANDS CONTAINING MODIFIED NUCLEOTIDES

This application is a Continuation of U.S. patent application Ser. No. 08/430,709, filed Apr. 27, 1995 entitled High Affinity Nucleic Acid Ligands Containing Modified Nucleotides, now U.S. Pat. No. 5,660,985. U.S. application Ser. No. 08/430,709 is a Continuation of U.S. patent application Ser. No. 08/117,991 filed Sep. 8, 1993, entitled High Affinity Nucleic Acid Ligands Containing Modified Nucleotides, now abandoned, which application is a Continuation-in-Part of U.S. patent application Ser. No. 07/714,131, filed Jun. 10, 1991, entitled Nucleic Acid Ligands now U.S. Pat. No. 5,475,096 and U.S. patent application Ser. No. 07/536,428, filed Jun. 11, 1990, entitled Systematic Evolution of Ligands by Exponential Enrichment, now abandoned, U.S. patent application Ser. No. 07/973,333, filed Nov. 6, 1992, entitled Ligands of Thrombin, now U.S. Pat. No. 5,476,766, and U.S. patent application Ser. No. 07/964,624, filed Oct. 21, 1992, entitled Methods of Producing Nucleic Acid Ligands, now U.S. Pat. No. 5,496,938.

FIELD OF THE INVENTION

This invention relates to a method of preparing nucleic acid ligands. Specifically, this invention describes a method of preparing modified oligonucleotides capable of binding target molecules with high affinity. The modified oligonucleotides of the present invention contain one or more modified nucleotide bases, which include 5-X and/or 2'-Y substitutions in pyrimidine bases and 8-X and/or 2'-Y substitutions in purine bases. The invention includes nuclease-resistant oligonucleotide ligands containing the modified nucleotides of the present invention. The invention further includes methods for synthesizing the substituted nucleotides, bases and intermediates herein described. The general method utilized herein for preparing such nucleic acid ligands is called SELEX, an acronym for Systematic Evolution of Ligands for EXponential enrichment. The oligonucleotides of the present invention are modified by incorporation of chemically-modified nucleotide derivatives. The nucleotide derivatives incorporated into the oligonucleotides of the present invention also introduce means for incorporating additional functional groups into the nucleic acid ligands. This invention includes modified high affinity nucleic acid ligands which are single-stranded DNA and RNA ligands.

Specific examples are provided of oligonucleotides containing nucleotide derivatives chemically modified at the 5- and 2'-positions of pyrimidine. Further disclosed are specific RNA ligands to thrombin containing 2'-NH$_2$-modifications.

The modified oligonucleotides of the present invention increase the chemical diversity of the candidate mixture for the SELEX process, producing improved nucleic acid ligands to specific target molecules. In many cases, the modifications also provide the oligonucleotide with increased relative resistance to endonucleases in serum. The modified oligonucleotides of the present invention are useful as pharmaceuticals, diagnostic agents, and as part of gene therapy treatments.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding Proteins, it has become possible to describe some of the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from *E. coli*. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose function is to inactivate ribosomes in a target organism. A family of evolutionary related RNAs binds with specificity and decent affinity to nucleotides and nucleosides (Bass, B. and Cech, T. (1984) Nature 308:820–826) as well as to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et al. (1983) J. Biomol. Structure and Dynamics 1:539 and Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988). Proc. Natl. Acad. Sci. U.S.A. 85:1364–1368).

A type of in vitro evolution was reported in replication of the RNA bacteriophage Qβ. Mills, D. R. et al. (1967) Proc. Natl. Acad. Sci U.S.A. 58:217–224; Levisohn, R. and Spiegelman, S. (1968) Proc. Natl. Acad. Sci. U.S.A. 60:866–4872; Levisohn, R. and Spiegelman S. (1969) Proc. Natl. Acad. Sci. U.S.A. 63:805–811; Saffhill, R. et al. (1970) J. Mol. Biol. 51:531–539; Kacian, D. L. et al. (1972) Proc. Natl. Acad. Sci. USA 69:3038–3042; Mills, D. R. et al. (1973) Science 180:916–927. The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in *RNA: Catalysis, Splicing, Evolution*, Belfort and Shub (eds.), Elsevier, Amsterdam pp. 83–87; and Robertson and Joyce (1990) Nature 344:467) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using a deoxyoligonucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate.

The prior art has not taught or suggested more than a limited range of chemical functions for nucleic acids in their interactions with other substances: as targets for proteins that had evolved to bind certain specific oligonucleotide sequences; and more recently, as catalysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

U.S. patent application Ser. No. 07/536,428 filed Jun. 11, 1990, of Gold and Tuerk, entitled Systematic Evolution of Ligands by Exponential Enrichment, now abandoned, and U.S. patent application Ser. No. 07/714,131 filed Jun. 10, 1992 of Gold and Tuerk, entitled Nucleic Acid Ligands, now U.S. Pat. No. 5,475,096 (See also PCT Publication No. 91/19813) describe a fundamentally novel method for making a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by theory, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20–50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisionable target. However, in preferred embodiments the SELEX method is applied to situations where the target is a protein, including both nucleic acid-binding proteins and proteins not known to bind nucleic acids as part of their biological function. The SELEX Patent Applications include the selection of high affinity nucleic acid ligands that are inhibitors of the biological action of a protein. For example, U.S. Ser. No. 08/061,691, filed Apr. 22, 1993, entitled High-Affinity RNA Ligands of Basic Fibroblast Growth Factor (bFGF), now abandoned (See U.S. patent application Ser. No. 08/195,005, filed Feb. 10, 1994, entitled "High-Affinity RNA Ligands of Basic Fibroblast Growth Factor," now U.S. Pat. No. 5,459,015), discloses RNA ligand inhibitors of bFGF.

U.S. patent application Ser. No. 07/973,333, filed Nov. 6, 1992, entitled Ligands of Thrombin, now U.S. Pat. No. 5,475,766, herein specifically incorporated by reference, describes nucleic acid ligands to thrombin. Thrombin is a multifunctional serine protease that has important procoagulant and anticoagulant activities. As a procoagulant enzyme thrombin cleaves fibrinogen, activates clotting factors V, VIII, and XIII, and activates platelets. The specific cleavage of fibrinogen by thrombin initiates the polymerization of fibrin monomers, a primary event in blood clot formation. The central event in the formation of platelet thrombi is the activation of platelets from the "nonbinding" to the "binding" mode and thrombin is the most potent physiologic activator of platelet aggregation (Berndt and Phillips (1981) in Platelets in Biology and Pathology, J. L. Gordon, ed. (Amsterdam: Elsevier/North Holland Biomedical Press), pp. 43–74; Hanson and Harker (1988) Proc. Natl. Acad. Sci. U.S.A. 85:3184–3188; Eidt et al. (1989) J. Clin. Invest. 84:18–27). Thus, as a procoagulant, thrombin plays a key role in the arrest of bleeding (physiologic hemostasis) and formation of vasoocclusive thrombi (pathologic thrombosis).

As an anticoagulant thrombin binds to thrombomodulin (TM), a glycoprotein expressed on the surface of vascular endothelial cells. TM alters substrate specificity from fibrinogen and platelets to protein C through a combination of an allosteric change in the active site conformation and an overlap of the TM and fibrinogen binding sites on thrombin. Activated protein C, in the presence of a phospholipid surface, $Ca^{2+}$, and a second vitamin K-dependent protein cofactor, protein S, inhibits coagulation by proteolytically degrading factors Va and VIIIa. Thus the formation of the thrombin-TM complex converts thrombin from a procoagulant to an anticoagulant enzyme, and the normal balance between these opposing activities is critical to the regulation of hemostasis. It is therefore of interest to produce a high affinity nucleic acid ligand of thrombin capable of inhibiting its anticoagulant activity.

Native oligonucleotides are sensitive to degradation by nucleases. Two kinds of ribonucleases are known. The first, termed exonucleases, degrade an oligoribonucleotide sequentially from either the 3+- or the 5'-end. Exonucleases cleave the phosphodiester chain through catalyzing direct hydrolysis, with water as the attacking agent.

The more prevailing mode of degradation of oligoribonucleotides proceeds through catalysis by endonucleases. Endonucleases cleave RNA within the chain, 3' to the specific base they recognize. The mechanism of cleavage involves activation of the 2'-hydroxyl (2'-OH) to attack the phosphorous of the internucleotidic linkage (Saenger (1984) in: Principles of Nucleic Acid Structure, Springer Verlag, New York, p. 174). This initial step leads to chain cleavage with formation of the 2',3'-cyclic phosphate end on the 5'-product and a free 5'-OH end on the 3'-product. The major degradation of oligoribonucleotides in serum proceeds through pyrimidine-specific endonuclease (Pieken et al. (1990) Science 253:314).

The resistance of 2'-amino, 2'-deoxy pyrimidine homopolymers to degradation by pancreatic ribonuclease (RNAse A) has been reported. Both poly(2'-amino,2'-deoxyuridine) and poly(2'-amino,2'-deoxycytidine) are essentially completely stable towards RNAse A degradation. As expected, these polymers are readily degraded by snake venom phosphodiesterase, an enzyme that catalyzes water-hydrolysis of the phosphodiester backbone. The stability of 2'-amino,2'-deoxy pyrimidine containing oligonucleotides in rabbit serum is reported to be 1200-fold increased compared to unmodified oligoribonucleotides (Pieken et al. (1990) supra). This technology has been applied to the preparation of nuclease resistant hammerhead ribozymes (PCT Patent Application Publication WO 92/07065).

Oligonucleotides modified so as to exhibit resistance to nucleases are known to the art. For example, Ikehara et al. (1984) Eur. J. Biochem. 139:447 reported the synthesis of a mixed octamer containing a 2'-deoxy-2'-fluoroguanosine residue or a 2'-deoxy-2'-fluoroadenine residue. Ikehara et al. (1978) Nucleic Acids Res. 5:3315, showed that a 2'-chloro or bromo substituent in poly(2'-deoxyadenylic acid) provided nuclease resistance. Eckstein et al. (1972) Biochemistry 11:4336, showed that poly(2'-chloro-2'-deoxyuridylic acid) and poly(2'-chloro-2'-deoxycytidylic acid) are resistant to various nucleases. Inoue et al. (1987) Nucleic Acids Res. 15:6131, described the synthesis of mixed oligonucleotide sequences containing 2'-$OCH_3$ at every nucleotide unit. The mixed 2'-OCH3 substituted sequences hybridized to their RNAs as strongly at the non-substituted RNAs. Shibahara et al. (1987) Nucleic Acids Res. 17:239, also described the synthesis of mixed oligonucleotide sequences containing 2'-$OCH_3$ at every nucleotide unit.

The stability of oligoribonucleotides against endonuclease degradation may be achieved by replacement of the 2'-OH group of the ribose moiety with an alternate substituent such as an amino group or a fluoro group (Pieken et al. (1991) supra). Both 2'-amino and 2'-fluoro nucleoside 5-triphosphates are substrates for T7 RNA polymerase, albeit with somewhat decreased incorporation efficiency (Aurup et al. (1992) Biochemistry 31:9636–9641. Other 2'-substituted nucleotides such as 2'-O-methyl, 2'-O-alkyl, or 2'-deoxy nucleoside 5-triphosphates are not recognized as substrates by T7 RNA polymerase.

The 2'-amino,2'-deoxy pyrimidine nucleosides have been prepared previously (Verheyden et al. (1971) J. Org. Chem. 36:250; U.S. Pat. No. 3,755,295, issued Aug. 28, 1973). However, the reported method for preparation of the crucial 2'-azido,2'-deoxyuridine precursor is laborious and time consuming, with only moderate yields.

SUMMARY OF THE INVENTION

The present invention includes methods for producing high affinity nucleic acid ligands which incorporate chemically-modified nucleotides. In one embodiment of the method of the present invention, SELEX is performed with a candidate mixture of oligonucleotides containing modified nucleotides. In another embodiment of the method of the present invention, SELEX is performed with a candidate mixture of oligonucleotides not containing modified nucleotides and the selected high affinity ligands are subsequently modified by incorporation of modified nucleotides. Incorporation of modified nucleotides into oligonucleotides provides means for introducing additional functional groups into the nucleic acid ligands via the modified nucleotides. Thus, the method of the present invention provides increased enrichment of the chemical diversity of a nucleic acid candidate mixture from which ligands to specific targets are identified through the SELEX process. Further, the method of the present invention provides nucleic acid ligands with increased in vivo stability relative to the non-modified ligand.

The present invention includes oligonucleotides containing one or more modified bases. The modified pyrimidine bases of the present invention have substitutions of the general formula 5-X and/or 2'-Y, and the modified purine bases have modifications of the general formula 8-X and/or 2'-Y. The group X includes the halogens I, Br, Cl, or an azide or amino group. The group Y includes an amino group, fluorine, or a methoxy group as shown in FIG. 1. Other functional substitutions that would serve the same function may also be included.

The oligonucleotide ligands of the present invention may have one or more X-modified bases, or one or more Y-modified bases, or a combination of X- and Y-modified bases. The present invention encompasses derivatives of these substituted pyrimidines and purines such as 5'-triphosphates, and 5'-dimethoxytrityl, 3'-β-cyanoethyl, N,N-diisopropyl phosphoramidites with isobutyryl protected bases in the case of adenosine and guanosine, or acyl protection in the case of cytosine. Further included in the present invention are oligonucleotides bearing any of the nucleotide analogs herein disclosed. The present invention encompasses specific nucleotide analogs modified at the 5 and 2' positions, including 5-(3-aminoallyl)uridine triphosphate (5-AA-UTP), 5-(3-aminoallyl)deoxyuridine triphosphate (5-AA-dUTP), 5-fluorescein-12-uridine triphosphate (5-F-12-UTP), 5-digoxygenin-11-uridine triphosphate (5-Dig-11-UTP), 5-bromouridine triphosphate (5-Br-UTP), 2'-amino-uridine triphosphate (2'-$NH_2$-UTP) and 2'-amino-cytidine triphosphate (2'-$NH_2$-CTP), 2'-fluoro-cytidine triphosphate (2'-F-CTP), and 2'-fluoro-uridine triphosphate (2'-F-UTP).

Further included in the present invention are nuclease-resistant oligonucleotide ligands containing the modified nucleotides of the present invention.

The non-limiting examples provided in the present disclosure are explanatory and exemplary of the method of the present invention.

BRIEF DESCRIPTION OF THE FIGURES

FIGS. 6A and 6B depict nucleotide sequences of RNA ligands isolated by SELEX for human thrombin. Each sequence is divided into 3 blocks from left to right: 1) the 5' fixed region, 2) the 30 base pair (30N) variable region, and 3) the 3' fixed region. FIG. 6A depicts 2'-OH RNA ligands separated into class I and II. FIG. 6B depicts 2'-$NH_2$ RNA ligands separated into groups I, II, and III.

FIGS. 7A–7F show proposed secondary structures of RNA ligands. FIG. 7A shows the sequence of the class I 2'-OH RNA clone 16. FIG. 7B shows the sequence of the class II 2'-OH RNA clone 27. FIG. 7C shows the sequence of the group I 2'-$NH_2$ RNA clone 32. FIG. 7D shows the sequence of the group II sub A 2'-$NH_2$ RNA clone 37, and FIG. 7E shows the sequence of the sub B clone 17. FIG. 7F shows the sequence of the group III 2'-$NH_2$ RNA clone 29.

FIG. 8A shows thrombin binding curves for nonselected 30N3 RNA (•), and for the 2'-OH RNA ligand class I clone 16 (◊) and class II clone 27 (x). FIG. 8B shows the thrombin binding curves for 2'-$NH_2$-30N3 (nonselected) (•) and for 2'-$NH_2$ RNA ligand clones 32, 37, and 17 (◊).

DETAILED DESCRIPTION OF THE PREFERRED EMBODIMENTS

Figure 1:
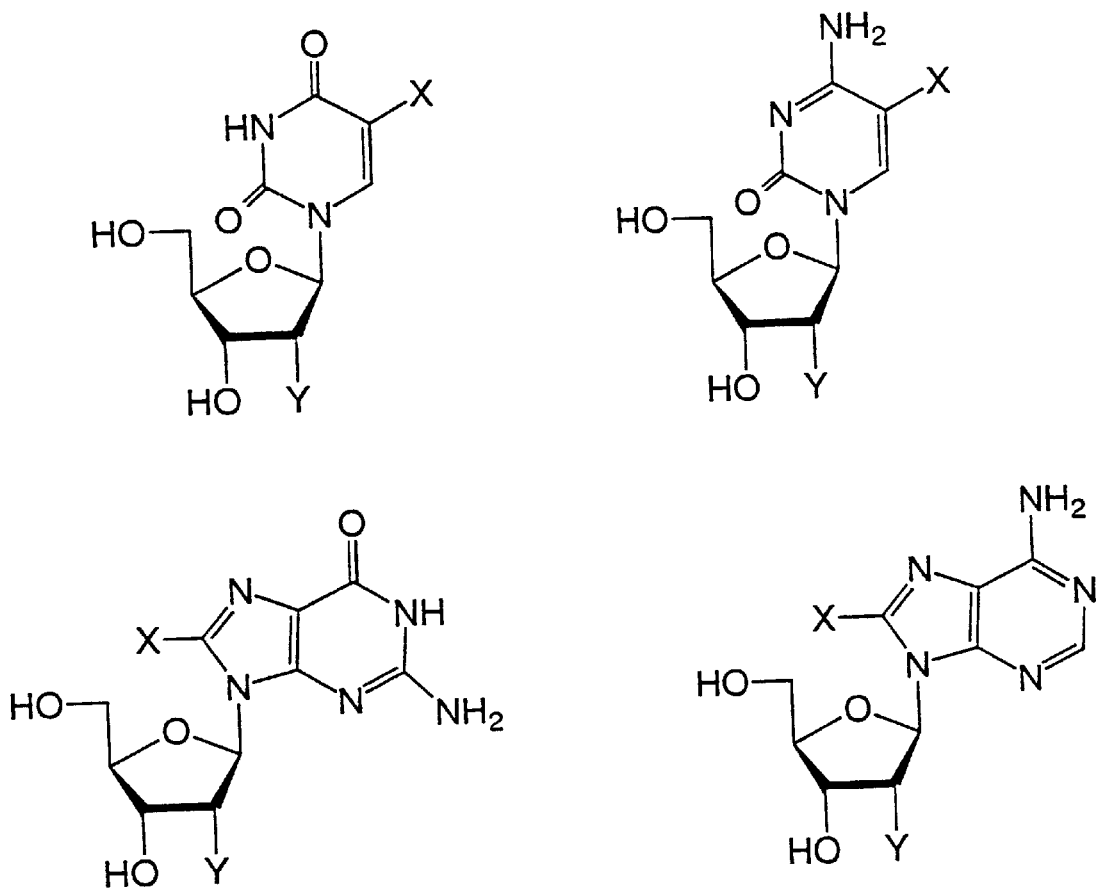
FIG. 1 illustrates some of the 2'- and 5-substituted nucleosides which may be utilized by the method of the present invention.

This application is an extension of the method for identifying nucleic acid ligands referred to as SELEX. The SELEX method is described in detail in U.S. patent application Ser. No. 07/714,131 filed Jun. 10, 1991 entitled Nucleic Acid Ligands, now U.S. Pat. No. 5,475,096, Ser. No. 07/536,428 filed Jun. 11, 1990 entitled Systematic Evolution of Ligands by EXponential Enrichment, now abandoned, and Ser. No. 07/964,624 filed Oct. 21, 1992, entitled Methods of Producing Nucleic Acid Ligands, now U.S. Pat. No. 5,496,938. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–10%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

SELEX delivers high affinity ligands of a target molecule. This represents a singular achievement that is unprecedented in the field of nucleic acids research. The present invention is directed at methods for producing improved nucleic acid ligands. In one embodiment of the method of the present invention, SELEX is performed with a candidate mixture of oligonucleotides containing one or more modified nucleotides. The presence of the modified nucleotides increases the chemical diversity of the candidate mixture, allowing improved ligands to a particular target molecule to be identified. In another embodiment of the method of the present invention, nucleic acid ligands selected through the SELEX process are modified by incorporation of modified nucleotides. The presence of modified nucleotides in the nucleic acid ligands enhances their in vivo resistance to degradation by nucleases and may further enhance other desirable characteristics.

In order to produce nucleic acids desirable for use as pharmaceuticals, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target. Important modifications or derivatizations of the ligand to which the method of the present invention are directed are those that confer resistance to degradation and clearance in vivo during therapy. Further improvements conferred by the method of the present invention may include enhanced capacity to cross various tissue or cell membrane barriers, or any other accessory properties that do not significantly interfere with affinity for the target molecule.

The increased chemical diversity achieved by carrying out SELEX with nucleotide analogs can introduce ligand properties such as enhanced stability against nucleases, incorporation of reporter groups, introduction of moieties capable of covalent crosslinking to a target, or introduction of intraligand crosslinks for the generation of stable conformers and novel oligonucleotide shapes.

Introduction of 2'-amino,2'-deoxy pyrimidines into the SELEX candidate mixture library requires preparation of their 5'-triphosphate derivatives. This is the form that is recognized as a substrate for DNA-dependent RNA polymerases or for DNA-dependent DNA polymerases. Furthermore, analogs also have to be prepared as the phosphoramidite in order to be incorporated into the final oligonucleotide ligand by automated chemical synthesis. These derivatives have been described, along with their method of preparation (Aurup et al. (1992) Biochemistry 31:9636). The synthesis of oligonucleotides containing 2'-amino,2'-deoxy pyrimidines by T7 RNA polymerase transcription of DNA templates has also been previously reported (Aurup et al. (1992) supra; Pieken et al. (1990) supra). Homopolymers of the 2'-amino,2'-deoxy pyrimidine nucleotides have also been prepared by polymerization of their 5'-diphosphate derivatives (Hobbs et al. (1973) supra). Oligoribonucleotides containing 2'-amino,2'-deoxy pyrimidines have also been prepared by automated solid phase synthesis. The trifluoroacetyl group has been used for protection of the 2'-amino group in preparation of phosphoramidite monomers (Pieken et al. (1990) supra).

As described above and in the SELEX patent applications, the SELEX technology identifies specific high affinity oligonucleotide ligands to a given molecular target by iterative enrichment from a vast pool of species. In one embodiment of the present invention, the amplified oligodeoxyribonucleotide sequences are transcribed to its oligoribonucleotide homolog with T7 RNA polymerase. Thus, during each step in the enrichment process, the library is reassembled from its nucleoside triphosphate building blocks. This feature allows the introduction of chemically modified nucleoside triphosphates, and thus the enrichment of ligands bearing chemical functionalities not found in native RNA. Examples of such modifications include chemical substitutions at the ribose and/or phosphate positions of a given RNA sequence. See, e.g., Cook et al. PCT Application WO 9203568; U.S. Pat. No. 5,118,672 of Schinazi et al.; Hobbs et al. (1973) Biochem 12:5138; Guschlbauer et al. (1977) Nucleic Acids Res. 4:1933; Shibahara et al. (1987) Nucl. Acids. Res. 15:4403; Pieken et al. (1990) supra, each of which is specifically incorporated herein by reference.

The increased chemical diversity achieved by the method of the present invention requires the chemical synthesis of a number of compounds. It is desirable to have a highly divergent synthetic methodology at hand that allows preparation of a variety of desired nucleotide analogs from a common intermediate. These analogs in all cases need to infer nuclease resistance to the oligonucleotide.

A large variety of modifying groups can be introduced to the 5-position of pyrimidines. Such methods are described in U.S. patent application Ser. No. 08/076,735, filed Jun. 14, 1993, entitled Method for Palladium Catalyzed Carbon-Carbon Coupling and Products, now U.S. Pat. No. 5,428,149, herein specifically incorporated by reference. The process described in U.S. Pat. No. 5,428,149 requires the 5-iodo or 5-bromo pyrimidine precursor. In order to generate base-modified pyrimidines that are also nuclease resistant, it is desirable to depart from a 2'-modified precursor for the coupling technology (U.S. Pat. No. 5,428,149).

5-iodo-2'-amino, 2'-deoxyuridine has been prepared previously (Verheyden et al. (1971) J. Org. Chem. 36:250). It has not been applied to the uses discussed herein. The 5-iodo,2'-deoxyuridine is introduced into the SELEX library of candidate oligonucleotides as the 5'-triphosphate derivative. The 5-iodo substituent is not compatible with the reaction conditions used in standard phosphorylation of 5-iodo,2'amino,2'-deoxy pyrimidines. Instead, the 5'-triphosphate derivative, which has not been previously described, is prepared from the 2'-amino,2'-deoxy pyrimidine 5'-triphosphate by mercuration of the 5-position (Dale et al. (1975) Biochemistry 14:2447) with subsequent iodination (Dale et al. (1975) Nucleic Acids Res. 2:915). These modified bases are central intermediates in the generation of base-modified nuclease resistant oligonucleotide ligands.

The modified nucleic acid ligands of the present invention may include one or more modified nucleotides. The proportion of modified to non-modified nucleotides contained in the nucleic acid ligands of the present invention may range from 1–100%.

In one embodiment of the method of the present invention wherein SELEX is performed with a library candidate mixture of oligonucleotides containing modified nucleotides, the desired amount of modified nucleotide incorporation in the oligonucleotides is achieved by including one or more modified nucleotides in the oligonucleotide synthesis mixture.

In a second embodiment of the method of the present invention, wherein one or more modified nucleotides are incorporated into a non-modified nucleotide-containing nucleic acid ligand identified through SELEX, SELEX is performed to completion with an initial candidate mixture of 2'-OH oligonucleotides, such that high-affinity nucleic acid ligands or family of ligands to a target molecule are identified. These ligands are then transcribed in the presence of modified nucleotides such that high-affinity ligands to the target molecule containing modified nucleotides are produced. The present invention includes oligonucleotide ligands modified at specific positions. Nucleic acids ligands containing modified nucleotides at specific positions may be produced by synthesis.

In another embodiment of the method of the present invention, SELEX is performed for a few selection rounds but not to completion, such that a candidate mixture of 2'-OH oligonucleotides is selected for partially enhanced affinity to the target molecule. Modified nucleotides are then incorporated into the partially-selected oligonucleotides by transcription in the presence of modified nucleotides.

Figure 2:
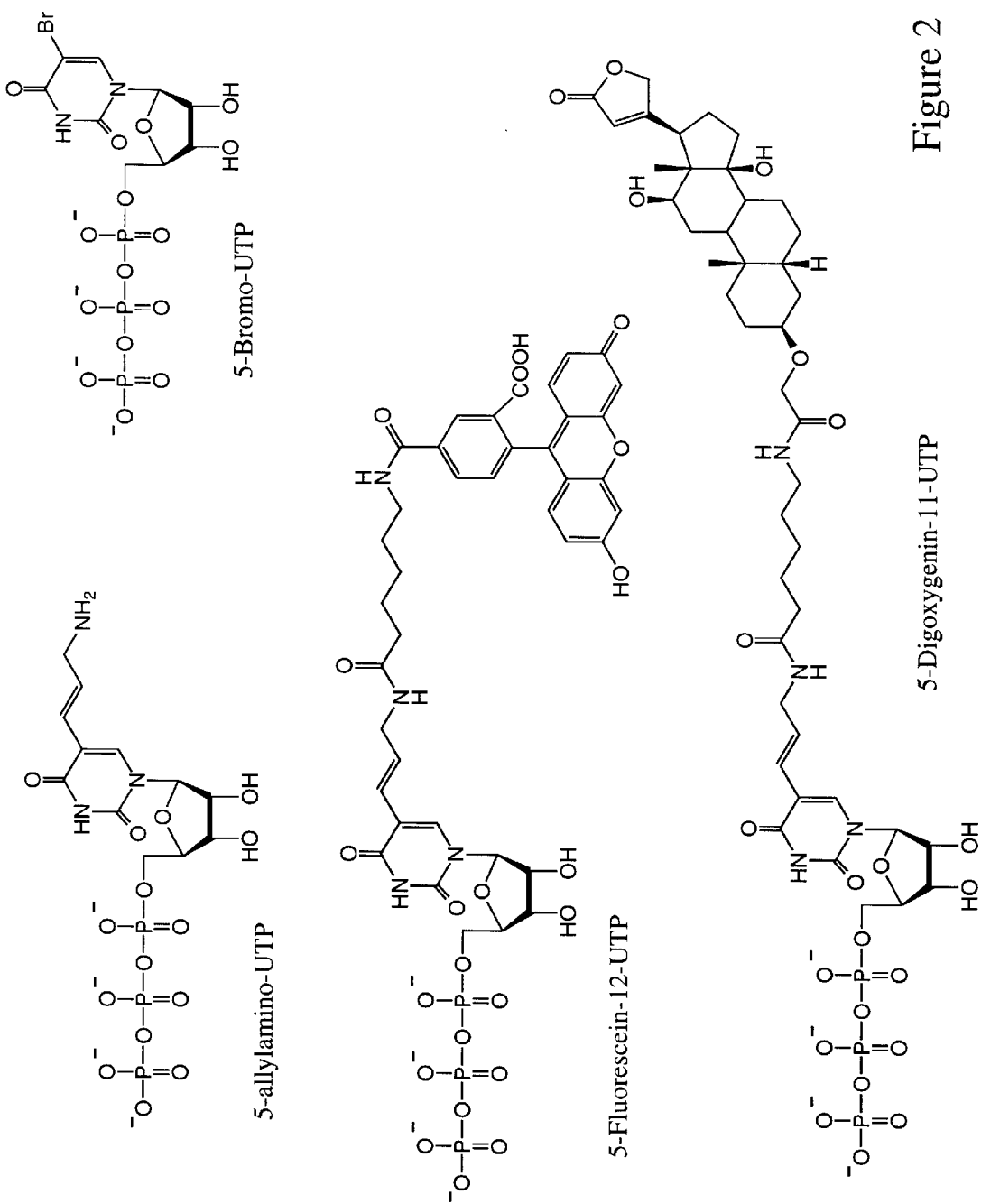
FIG. 2 illustrates the structures of 5-allylamino-UTP (5-AA-UTP), 5-bromo-UTP (5-Br-UTP), 5-fluorescein-12-UTP (5-F-12-UTP), 5-digoxygenin-11-UTP (5-Dig-11-UTP).

In order to be useful in the existing SELEX protocol, the modified nucleotides must meet the following criteria: 1) in their triphosphate forms they must be substrates for polymerase(s), and 2) the resulting modified oligonucleotides must be templates for amplification. Example 2 demonstrates that four prototypic 5-modified uridines meet the above requirements and can be used in SELEX. 5-AA-UTP, 5-F-12-UTP, 5-Dig-11-UTP, and 5-Br-UTP, shown in FIG. 2, are incorporated into RNA by the T7 RNA polymerase under standard transcription conditions. Modified transcripts were reversed transcribed into cDNA by AMV reverse transcriptase and amplified by PCR. These results show that modified nucleotides can be directly incorporated into the SELEX procedure.

As discussed above, 2'-amino modified pyrimidines and purines exhibit increased resistance to endonuclease activity. Example 3 describes SELEX selection of 2'-NH$_2$ ligands to the human thrombin. The affinities of SELEX identified 2'-OH and 2'-NH$_2$ ligands to thrombin are compared. While Example 3 describes SELEX identification of RNA ligands, the same procedure may be performed for the SELEX identification of DNA ligands to a specific target molecule. The only enzymatic requirement for DNA SELEX is that the modified deoxynucleoside triphosphates serve as substrates for Taq DNA polymerase or another suitable polymerase. It is known that digoxygenin-11-deoxyuridine triphosphate can be used as a replacement substrate for TPP in PCR (Lanzillo (1990) BioTechniques 8:621).

This invention includes the specific 2'-OH and 2'-NH$_2$ nucleic acid ligands of thrombin shown in FIGS. 6A and 6B. Specifically, this invention includes modified and non-modified nucleic acid sequences that are 1) substantially homologous to and that have substantially the same ability to bind thrombin as the specific nucleic acid ligands shown in FIGS. 6A and 6B. By substantially homologous, it is meant, a degree of primary sequence homology in excess of 70%, most preferably in excess of 80%. Substantially the same ability to bind thrombin means that the affinity is within two orders of magnitude of the affinity of the substantially homologous sequences described herein. It is well within the skill of those of ordinary skill in the art to determine whether a given sequence—substantially homologous to those specifically described herein—has substantially the same ability to bind thrombin.

As has been shown, sequences that have little or no primary sequence homology may still have substantially the same ability to bind the target molecule. It is clear that binding is controlled by the secondary or tertiary structure of the nucleic acid ligand. For these reasons, the present invention includes nucleic acid ligands that have substantially the same structural form as the ligands presented herein and that have substantially the same ability to bind thrombin as the modified and unmodified nucleic acid ligands shown in FIGS. 6A an 6B. Wherein substantially the same structure includes all nucleic acid ligands having the common structural elements shown in FIGS. 7A–7F that lead to the affinity to thrombin. This invention further includes ligands containing a variety of modified nucleotides, such as 2'-fluoro modifications.

Example 4 describes a novel method for the synthesis of 5-iodo,2'-amino deoxyuridine. The synthesis of the intermediate 5-iodo,2'-amino deoxyuridine, shown in FIG. 9, achieves a greater yield of the compound over the prior art method with fewer synthetic steps.

Example 5 describes the synthesis of 5-iodo,2'-amino,2'-deoxy pyrimidine 5'-triphosphate. 5-iodo,2'-amino,2'-deoxy pyrimidine 5'-triphosphates cannot be prepared from their 5-iodo,2'-amino,2'-deoxy pyrimidine nucleoside precursors because the conditions employed in the phosphorylation reaction are not compatible with the 5-iodo group. However, they may be prepared from the 2'-amino,2'-deoxy pyrimidine 5'-triphosphates by mercuration and subsequent iodination of the C-5 position.

Example 6 describes the in vivo stability of 2'-NH$_2$ modified ligands of thrombin.

The method of the present invention further includes incorporation of functional groups into oligonucleotides via the modified nucleotides. One of the products of the SELEX procedure is a consensus of primary and secondary structures that enables the chemical or enzymatic synthesis of oligonucleotide ligands whose design is based on that consensus. Because the replication machinery of SELEX requires that rather limited variation at the subunit level (ribonucleotides, for example), such ligands imperfectly fill the available atomic space of a target molecule's binding surface. However, these ligands can be thought of as high-affinity scaffolds that can be derivatized to make additional contacts with the target molecule. In addition, the consensus contains atomic group descriptors that are pertinent to binding and atomic group descriptors that are coincidental to the pertinent atomic group interactions. The present invention further includes nucleic acid ligands containing additional functional groups introduced via the modified nucleotides. A strategy for introduction of functional groups is described in Example 7.

EXAMPLE 1

Experimental Procedures

SELEX. Essential features of the SELEX protocol have been described in detail in previous papers (Tuerk & Gold (1990) Science 249:505; Tuerk et al. (1992a) Proc. Natl. Acad. Sci. U.S.A. 89:6988; Tuerk et al. (1992b) in Polymerase Chain Reaction (Ferre, F., Mullis, K., Gibbs, R. & Ross, A., eds.) Birkhauser, N.Y.). Briefly, DNA templates for in vitro transcription (that contain a region of thirty random positions flanked by constant sequence regions) and the corresponding PCR primers were synthesized chemically (Operon). The random region was generated by utilizing an equimolar mixture of the four nucleotides during oligonucleotide synthesis. The two constant regions were designed to contain PCR primer annealing sites, a primer annealing site for cDNA synthesis, T7 RNA polymerase promoter region, and restriction enzyme sites that allow cloning into vectors.

Nitrocellulose Filter Binding Assay

Oligonucleotides bound to proteins can be effectively separated from the unbound species by filtration through nitrocellulose membrane filters (Yarus & Berg (1970) Anal. Biochem. 35:450; Lowary & Uhlenbeck (1987) Nucleic Acids Res. 15:10483; Tuerk & Gold (1990) supra). Nitrocellulose filters (Millipore, 0.45 μm pore size, type HA) were secured on a filter manifold and washed with 4–10 ml of buffer. Following incubations of $^{32}$P-labeled RNA with serial dilutions of the protein (5–10 min) at 37° C. in buffer (PBS) containing 0.01% human serum albumin (HSA), the solutions were applied to the filters under gentle vacuum in 45 μl aliquots and washed with 5 ml of PBS. The filters were then dried under an infrared lamp and counted in a scintillation counter.

Cloning and Sequencing

Individual members of the enriched pools were cloned into pUC18 vector and sequenced as described (Schneider et al. (1992) J. Mol. Biol. 228:862–869; Tuerk & Gold (1990) supra).

EXAMPLE 2

Modified RNAs

Incorporation of 5-modified Uridines into RNA

Figure 3:
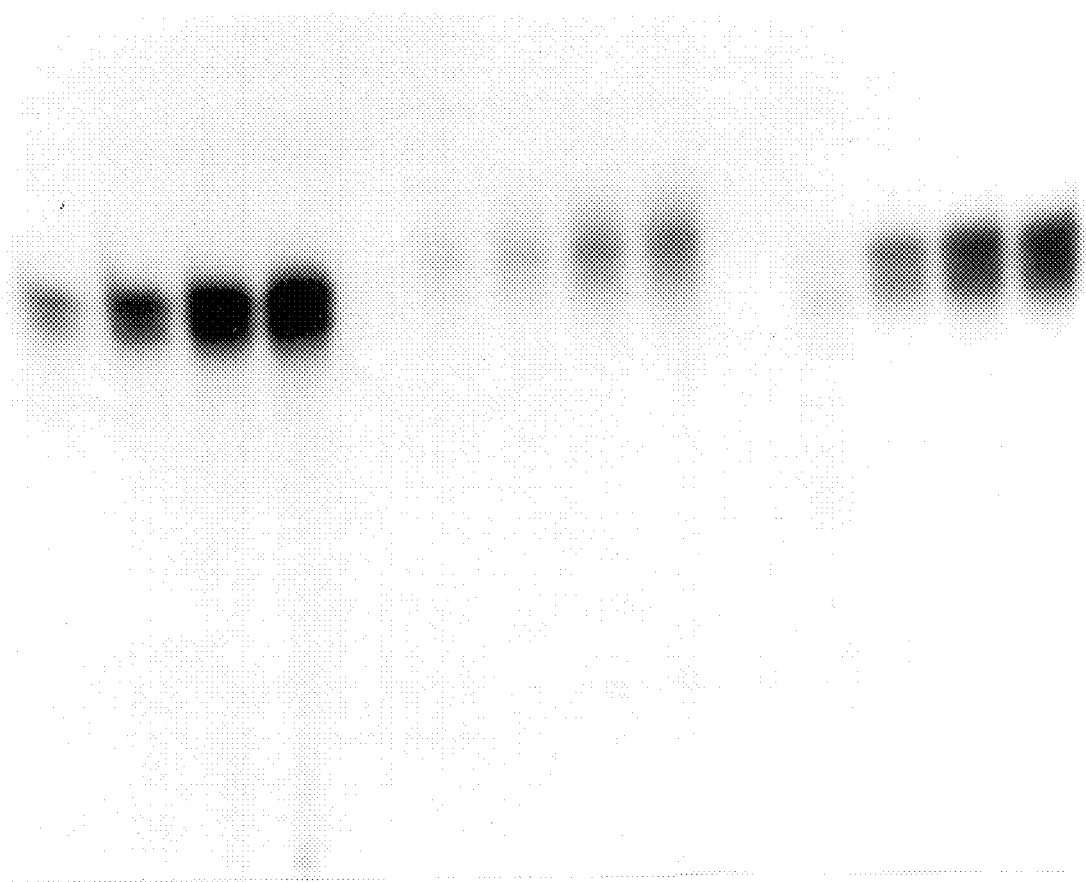
FIG. 3 shows the autoradiogram of a 15% denaturing polyacrylamide gel for transcription of an 87-mer of defined sequence. Four time points are 0.5, 1.0, 2.0, and 3.0 hours.
Figure 4:
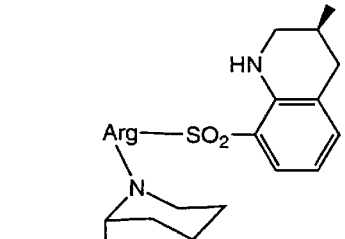
FIG. 4 shows examples of side chains on 5-AA-UTP (for RNA SELEX) or 5-AA-dUTP (for DNA SELEX) that direct the binding of an oligonucleotide to a specific site of a target.
Figure 4:
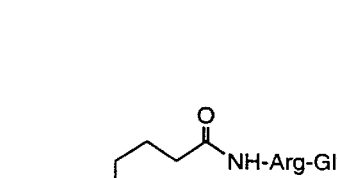
Figure 4:
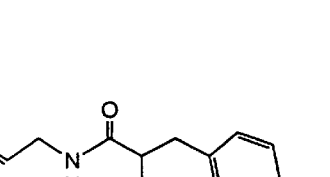

Four prototypic 5-modified uridines, 5-AA-UTP, 5-F-12-UTP, 5-Dig-11-UTP, and 5-Br-UTP (shown in FIG. 2) were incorporated into RNA by the T7 RNA polymerase under standard transcription conditions (40 mM Tris-Cl, pH 8.0, 12 mM MgCl$_2$, 5 mM DTT, 1 mM spermidine, 0.002% Triton X-100, 4% PEG, 37° C.). Autoradiogram of a 15% denaturing polyacrylamide gel showing products of transcription done with UTP, 5-AA-UTP, and 5-Br-UTP is shown in FIG. 3. The efficiency of transcription was estimated from the total amounts of $^{32}$P-radiolabelled transcript produced after three hours of incubation with 2 mM ribonucleotide triphosphates, 100 nM double-stranded DNA template, and 5 units/μl of T7 RNA polymerase (NEB). 5-AA-UTP, 5-F-12-UTP, 5-Dig-11-UTP, and 5-Br-UTP were incorporated with 28%, 51%, 23%, and 50% efficiency, respectively, as compared to UTP. No transcription was detectable when UTP was omitted from the transcription mixture.

Modified transcripts containing 5-AA-UTP, 5-F-12-UTP, 5-Dig-11-UTP, or 5-Br-UTP were reverse transcribed into cDNA by AMV reverse transcriptase with efficiencies comparable to that of the unmodified RNA (done in 50 mM Tris, pH 8.3, 60 mM NaCl, 6 mM Mg(OAc)$_2$, 10 mM DTT, 37° C.) (data not shown). These cDNAs were then amplified by PCR. Sequencing of the PCR products derived from UTP, 5-AA-UTP, and 5-Br-UTP transcriptions revealed that identical products were obtained in all three cases. These results show that modified nucleotides can be directly incorporated into the RNA SELEX procedure.

EXAMPLE 3

2'-NH$_2$ RNA Ligands for Thrombin

2'-NH$_2$ modified RNA

RNA was transcribed with T7 RNA polymerase from double-stranded DNA in a reaction containing ATP, GTP, 2'-NH$_2$-UTP, and 2'-NH$_2$-CTP.

2'-OH and 2'-NH$_2$ RNA SELEX for Thrombin

SELEX experiments with thrombin were done with 2'-OH RNA and 2'-NH$_2$ RNA under almost identical conditions. A 30N3 template/primer set was used in both experiments. SELEX with 2'-OH RNA was conducted in 1X binding buffer (50 mM Tris-Cl, pH 7.7, 100 mM NaCl, 1 mM MgCl$_2$, and 1 mM DTT). SELEX with 2'-NH$_2$ RNA was conducted in 1X binding buffer without DTT. Approximately equimolar concentrations of RNA and protein were used in the 2'-OH RNA experiment; 2'-NH$_2$ bulk RNA had a higher starting affinity for thrombin (kD$_{2'-OH}$=>1.0×10$^{-6}$; kD$_{2'-NH_2}$, =<1.0×10$^{-6}$) and thus the protein concentrations used in this SELEX experiment were higher. Both of the experiments began with the same concentration of RNA (2.5×10$^{-7}$) and were done at equimolar RNA and protein, or protein excess.

Sequence

Two predominant classes (2'-OH) or groups (2'-NH$_2$) of sequences were obtained in each experiment (FIGS. 6A and 6B). For the 2'-OH RNAs, class I contained 22/26 clones, and class II contained 6/28 clones. For the 2'-NH$_2$ RNAs, group I contained 15/47 clones, group II contained 30/45 clones, and group III contained 2/47 clones. Each class showed remarkable homology within the 30N region.

Secondary Structural Analysis

Secondary structures were predicted for the high affinity 2'-OH and 2'-NH$_2$ RNA ligands to thrombin shown in FIGS. 7A–7F. Clone 17 is representative of the A subgroup of the group II 2'-NH$_2$ ligands. Clone 16 is representative of the class I ligands of the 2'-OH ligands and clone 27 is representative of the class II ligands of the 2'-OH ligands.

Binding Analysis

Figure 8A:
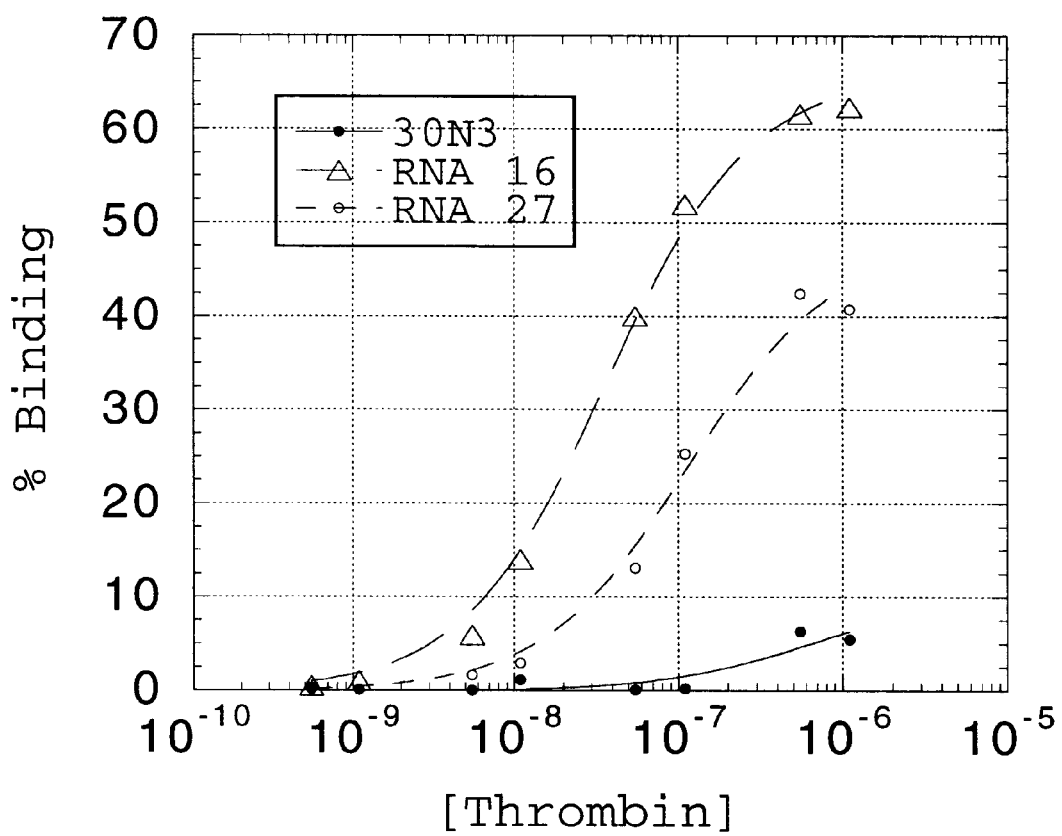
FIGS. 8A and 8B binding curves for thrombin ligands.
Figure 8B:
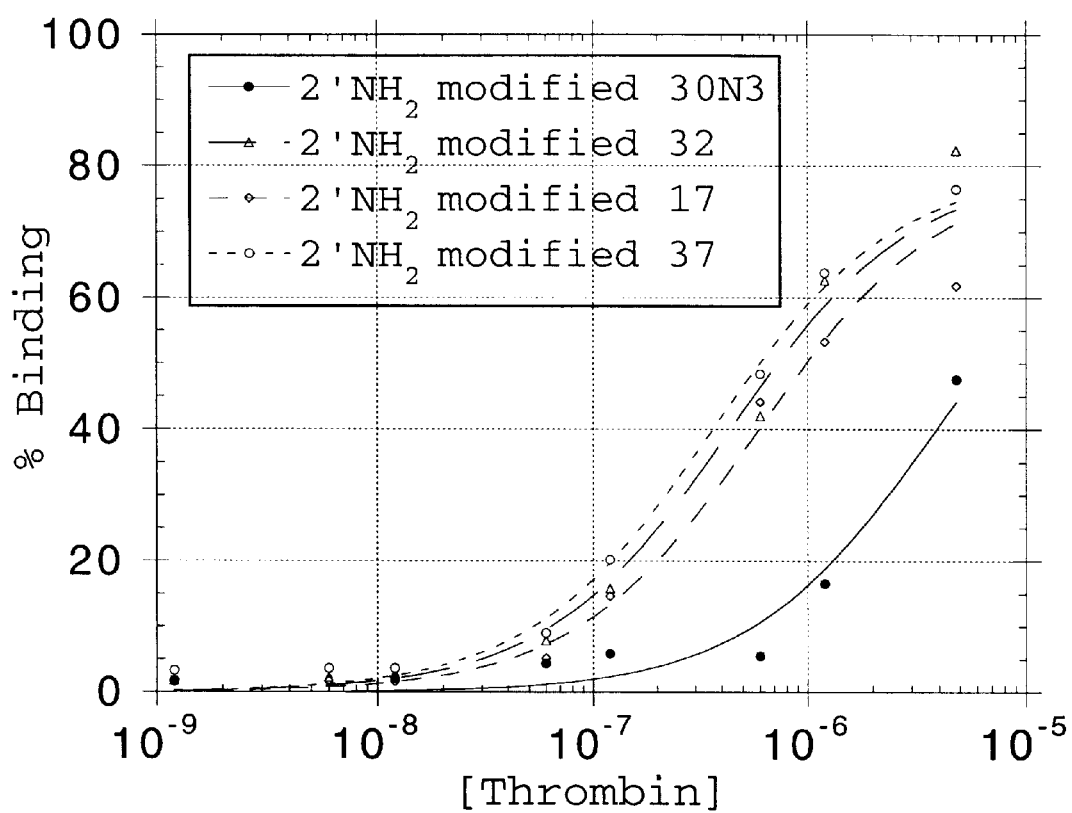

All binding analyses were done by nitrocellulose filter binding. Binding curves as determined by increasing protein concentration in the presence of a fixed RNA concentration lower than the protein concentration are shown for the 2'-OH ligands in FIG. 8A and for the bulk 2'-NH$_2$ ligands in FIG. 8B. Under these conditions, the RNAs 16 and 27 have kDs of 30 nM and 60 nM, respectively. The kD for the bulk 2'-NH$_2$ round 15 ligands which had been sequenced is approximately 200 nM.

EXAMPLE 4

Figure 9:
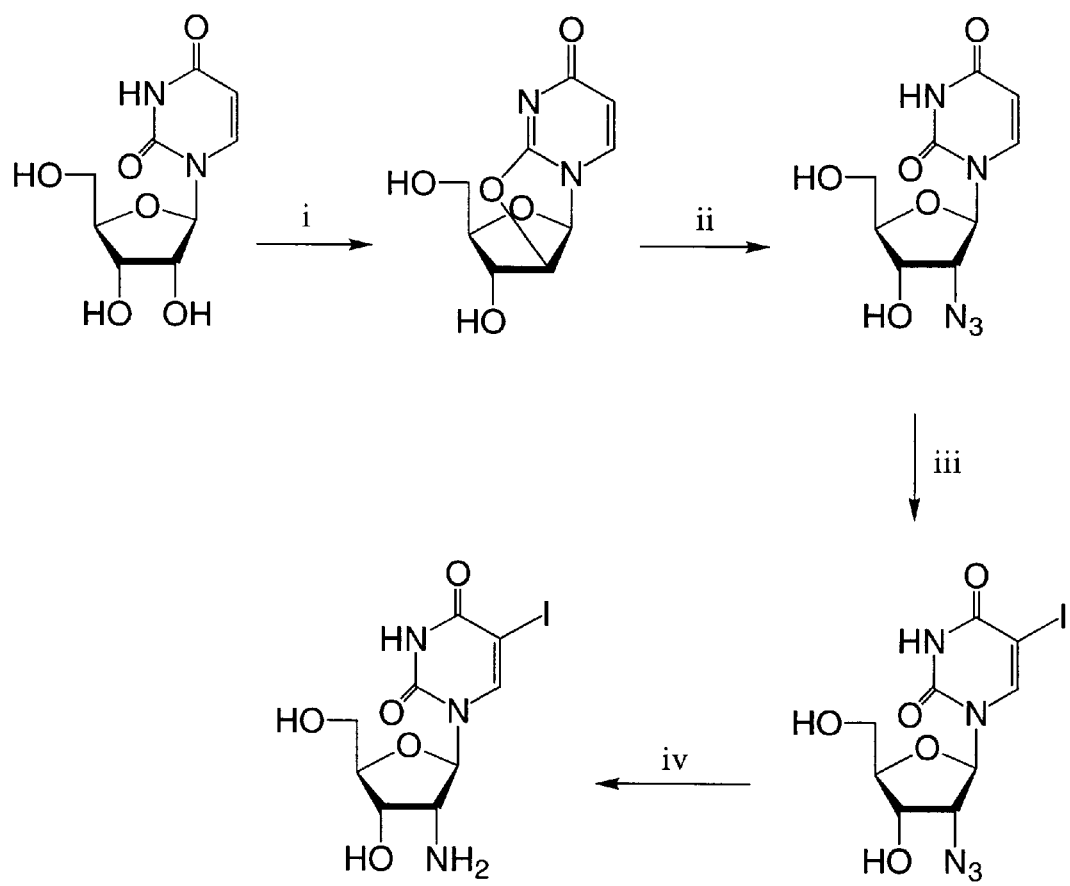
FIG. 9 illustrates the four step synthesis of 5-iodo-2'-amino,2'-deoxyuridine.

Synthesis of 5-Iodo,2'-Amino Deoxyuridine 5-iodo,2'-amino,2'-deoxyuridine has been previously prepared from uridine (Verheyden et al. (1971) supra). The reported synthesis involved five steps and gave the desired compound in an overall yield of 3%. Presented herein is a method of preparing 5-iodo,2'-amino,2'-deoxyuridine in four steps from uridine with an overall yield of 46%. The synthesis of 5-iodo,2'-amino,2'-deoxyuridine is shown in FIG. 9. In the method presented below, uridine is initially dehydrated to the 2,2'-anhydrouridine by the standard method (Verheyden et al. (1971) supra) in 92% yield. This intermediate is then converted to the 2'-azido,2'-deoxyuridine in 84% yield according to Example 7 below (Synthesis of 2'-Azido-2'-Deoxyuridine (ADU)). ADU is iodinated at the C-5 position without protection of the 5'- and 3'-OH groups in 76% yield in adaptation of the method of Robins et al. (1982) Can. J. Chem. 60:554. Reduction of the 5-iodo,2'-amino,2'-deoxyuridine with triphenylphosphine gave 78% yield of the desired compound.

Synthesis of 2,2'-Anhydrouridine

To a suspension of uridine (200 g, 819 mmoles) in hexamethylphosphoramide (HMPA) (400 ml) was added sodium bicarbonate (5.3 g, 63.1 mmoles, 0.077 equivalents (eq.)) and diphenyl carbonate (228.1 g, 1064.7 mmoles, 1.3 eq.). The mixture was heated to 135° C. for 11 h. After cooling to room temperature, diethyl ether (2 l) was added and the precipitate was filtered off. The solid was washed three times with ether (3×1 l). Water (1 l) was added to the filtrate, the aqueous layer was separated and extracted three times with methylene chloride (3×1 l). The aqueous phase was evaporated to dryness. The combined solids were recrystallized from hot methanol to yield 170 g (92%) of 2,2'-anhydrouridine. The spectral properties agreed with those reported in the literature (Hampton and Nichol (1966) Biochemistry 5:2076).

Synthesis of 2'-Azido,2'-deoxyuridine

The synthesis of 2'-azido-2'-deoxyuridine (ADU) has been previously published (Moffat et al. (1971) J. Org. Chem. 36:250). According to this procedure, anhydrouridine is treated with 7.1 equivalents of lithium azide in HMPA at 150° C. The desired product is obtained in only 50% yield after separation from a number of by-products. It is desirable to have a process by which ADU is synthesized in high yield without the necessity of further purification by chromatographic processes. Furthermore, it is desirable to avoid the use of HMPA, a known carcinogen.

A procedure was developed which utilizes an in situ generation of lithium azide in the presence of N',N',N",N"-tetramethylethylenediamine (TMEDA) in DMF at 100–110° C. When anhydrouridine is allowed to react with 1.5 equivalents of this lithium azide:TMEDA complex in DMF at 105–110° C. for 24–48 h, ADU is formed in high yield as the sole product. The process described represents a substantial improvement over the previously known method.

Lithium fluoride (0.93 g, 36 mmol) was suspended in 20 ml of DMF heated to 105° C. To the stirred suspension was added 20 ml of TMEDA followed by azidotrimethylsilane (4.15 g, 36 mmol). After stirring for 30 min, anhydrouridine (4.52 g, 20 mmol) was added and the reaction allowed to proceed for 48 h. The solvents were removed under vacuum and the residue co-evaporated from methanol three times. The residue was dissolved in 10 ml of methanol and 40 ml of ethyl acetate was added to precipitate most of the salt and residual starting material. The filtered solution was applied to 170 g of flash silica gel and eluted with 20% methanol/ethyl acetate. The product was obtained as an off-white solid (3.38 g, 63%): $^1$H NMR (DMSO-d$_6$, 300 MHz) δ 3.57 (dd, 1H, J=2.9, 12.2 Hz, H$_{5A'}$), 3.66 (dd, 1H, J=2.4, 1.2. Hz, H$_{5B'}$), 3.89 (dd, 1H, J=2.9, 4.4 Hz, H$_{4'}$), 4.05 (dd, 1H, J=5.4, H$_{2'}$), 4.30 (dd, 1H, J=4.4, 5.4 Hz, H$_{3'}$), 5,18 (br s, 1H, —OH), 5.67 (d, 1H, J=8.3 Hz), 5.88 (d, 1H, J=5.4 Hz, H$_{1'}$), 5.96 (br s, 1H, —OH), 7.86 (d, 1H, J=7.8 Hz), 11.4 (br s, 1H, NH); $^{13}$C NMR (DMSO-d$_6$, 75 MHz) δ 60.20, 64.57, 70.42, 85.21, 85.55, 102.03, 139.98, 150.40, 162.96; IR.

Synthesis of 5-Iodo,2'-azido,2'-deoxyuridine

To a solution of 2'-azido,2'-deoxyuridine (2.5 g, 9.3 mmoles) in methanol (20 ml) is added ICl (3.3 g, 20.5 mmoles, 2.2 eq.). The mixture is heated at 50° C. for 30 min. After cooling to room temperature, an equal volume of ether is added and the white precipitate is filtered off. The precipitate is stirred in methanolic ammonia (20 ml) at room temperature for 15 min, and then evaporated to dryness to yield 2.81 g (76%) of 5-iodo,2'-azido,2'-deoxyuridine. $^1$H NMR (300 MHz, methanol -d$_4$) δ 8.58 (s, 1H, H$_6$), 5.88 (d, 1H, H$_{1'}$, J$_{H1',H2'}$=3.5 Hz), 4.46 (t, 1H, H$_{3'}$, J=5.8 Hz), 4.11 (dd, 1H, H$_{2'}$, JH$_{1',H2'}$=3.9 Hz, JH$_{2',H3'}$=5.3 Hz), 4.01 (m, 1H, H$_{4'}$), 3.91 (dd, 1H, H$_{5'A}$ J$_{gem}$=12.3 Hz, J$_{H5',H4'}$=2.4 Hz) 3.76 (dd, 1H, H$_{5'B}$, J$_{gem}$=12.3 Hz, J$_{H5',H4'}$=2.4 Hz). $^{13}$C NMR (75 MHz, methanol-d$_4$) δ 163.03, 152.17, 146.50, 88.88, 86.18, 71.21, 67/67, 61.00, 48.15. FAB mass spectrum, (M+H) m/z 396.

Synthesis of 5-iodo,2'-amino,2'-deoxyuridine

To a solution of 5-iodo,2'-azido,2'-deoxyuridine (2.48 g, 6.3 mmoles) in dioxane (33 ml) is added triphenylphosphine (5.8 g, 22 mmoles, 3.5 eq.) and the mixture is stirred at room temperature for 1 h, during which time a white precipitate forms. The precipitate is collected and washed three times with diethyl ether (3×50 ml). The filtrate is evaporated to dryness, taken up in a minimum amount of dioxane, and stored at −20° C. for 48 h. The precipitate is collected and washed with diethyl ether. The combined precipitates gave 1.81 g of 5-iodo,2'-amino,2'-deoxyuridine (78% yield). The spectral properties agreed with those reported in the literature (Verheyden et al. (1971) supra).

EXAMPLE 5

Synthesis of 5-iodo,2'-amino,2'-deoxy pyrimidine 5'-triphosphates

The synthesis of 2'-amino,2'-deoxy pyrimidine 5'-triphosphates has not previously been reported in full detail. The 2'-amino,2'-deoxyuridine 5'-triphosphate was prepared via 5'-phosphorylation of 2'-azido,2'-deoxyuridine and subsequent reduction (Aurup et al. (1992) supra). This route requires protection of the 3'-OH group, which can only be achieved selectively with intermittent protection of the 5'-OH group. Herein described is a method of preparing the compound in only two steps from 2'-amino,2'-deoxyuridine.

Figure 10:
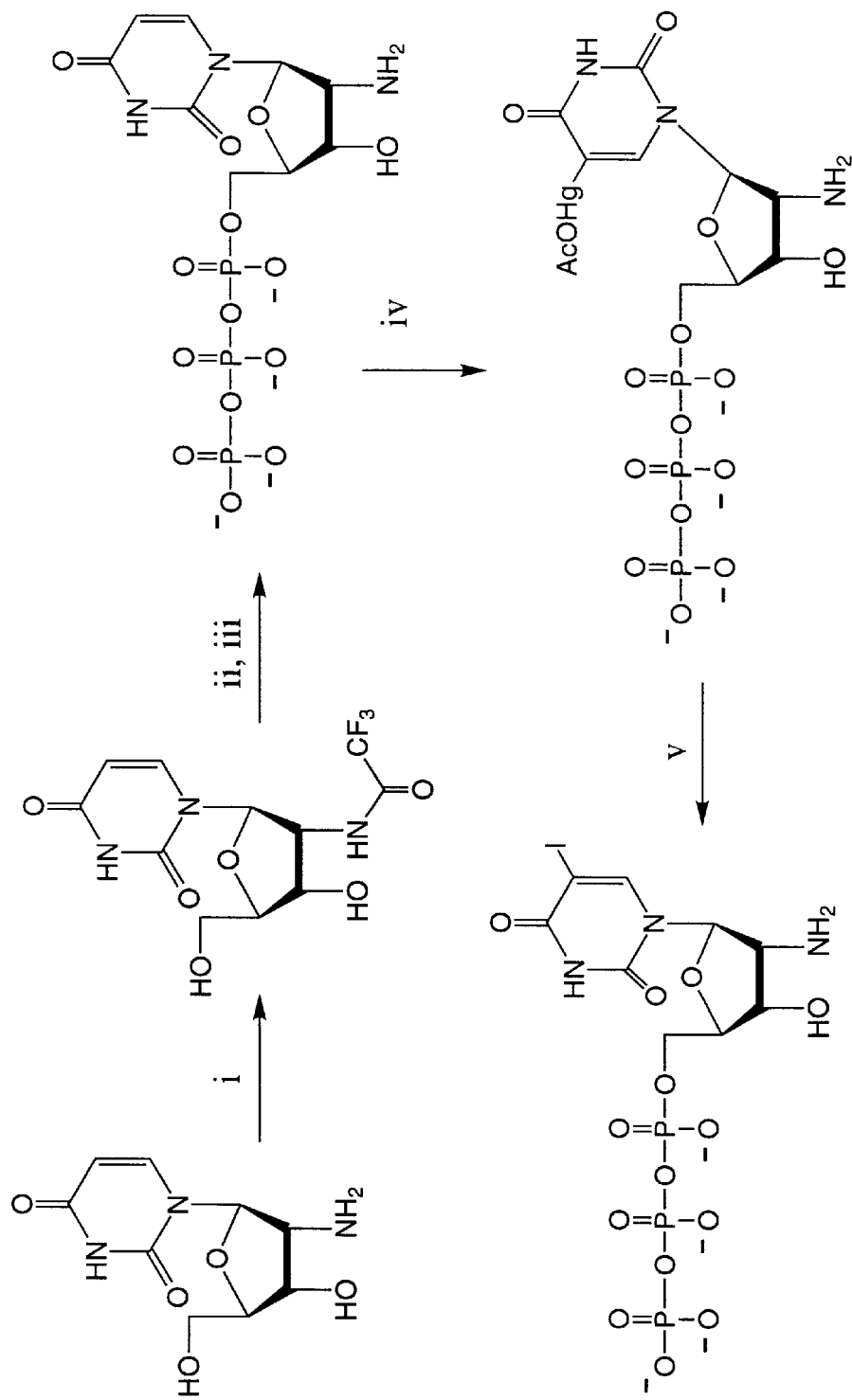
FIG. 10 shows the synthesis of 2'-amino,2'-deoxyuridine 5'-triphosphate.

The strategy relied on herein is based on the hypothesis that protection of the 3'-OH group is not necessary if the 2'-NH$_2$ group carries a protecting group that blocks the 3'-OH during phosphorylation. The synthesis of 2'-amino,2'-deoxyuridine 5'-triphosphate herein described is shown in FIG. 10.

The 2'-amino group of 2'-amino, 2'-deoxyuridine is trifluoroacetylated (Imazawa et al. (1979) J. Org. Chem. 44:2039) in 82% yield. This intermediate is phosphorylated at the 5'-position (Ludwig and Eckstein (1989) J. Org. Chem. 54:631) in 61% yield. The 5-iodo derivative of the 2'-amino,2'-deoxyuridine 5'-triphosphate was prepared by mercuration (Dale et al. (1975) supra) in a single step. Both 2'-amino,2'-deoxyuridine 5'-triphosphate and 5-iodo,2'-amino,2'-deoxyuridine 5'-triphosphate were shown to be substrates for T7 RNA polymerase. This has never been demonstrated before for the latter compound.

2'-Trifluoroacetylamino,2'-deoxyuridine

To a suspension of 2'-amino,2'-deoxyuridine (2.0 g, 8.22 mmoles) in methanol (150 ml) was added S-ethyl trifluorothioacetate (1.6 ml, 12.48 mmoles, 1.5 eq.). This mixture was stirred at room temperature overnight. Nitrogen was bubbled through the reaction mixture for 2 h to remove volatile thio-byproducts. The mixture was evaporated to dryness and the solid was recrystallized from methanol/chloroform to yield 2.3 g (82%) of 2'-trifluoroacetylamino, 2'-deoxyuridine. The analytical data agreed with the literature (Imazawa and Eckstein (1979) supra).

2'-Amino,2'-deoxyuridine 5'-triphosphate

2'-(N-trifluoroacetyl)amino,2'-deoxyuridine (230 mg, 0.68 mmoles) was dried under vacuum for 3 h prior to dissolution in anhydrous dioxane (2 ml) and anhydrous pyridine (0.68 ml). To this solution was added a freshly prepared solution of 2-chloro-4H-1,3,2-benzodioxaphosphorin-4-one in anhydrous dioxane (152 mg, dissolved to 1M). The reaction was stirred at room temperature for 10 min prior to addition of a solution of bis(tri-n-butylammonium) pyrophosphate in anhydrous DMF (2.04 ml, 1.02 mmoles, 1.5 eq.) and tributylamine (162 $\mu$l, 0.68 mmoles). After 15 min at room temperature an iodine solution was added (279 mg, 1% solution, pyridine/water 98:2 v/v). The mixture was stirred at room temperature for an additional 15 min and the excess iodine destroyed with aqueous NaHSO$_4$ (5% solution). The mixture was evaporated to dryness and the residue taken up in water (10 ml). After addition of concentrated ammonia (10 ml) the mixture set at room temperature for 1 h. The product was purified by DEAE Sephadex A25 (Pharmacia) chromatography (0–1M triethylammonium bicarbonate buffer). To remove excess buffer salt, the product was repeatedly concentrated from methanol to yield 364 mg (62%) tetrakis(triethylammonium)-2'-amino,2'-deoxyuridine 5'-triphosphate. $^1$ NMR (300 MHz, methanol -d$_4$) $\delta$ 7.21 (d, 1H, H$_6$, J$_{H6,H5}$=8.1 Hz), 5.33 (d, 1H, H1', J$_{H1',H2'}$=7.9 Hz), 5.05 (d, 1H, H$_5$, J$_{H6,H5}$=8.1 Hz), 3.82 (dd, H$_{3'}$, J$_{H3',H2'}$=5.3 Hz, J$_{H3',H4'}$=1.6 Hz, 3.49 (m, 1H, HA), 3.42 (m, 1H, H$_{4'}$), 3.38 (m, 1H, H$_{5'B}$), 3.08 (dd, 1H, H$_{2'}$, J$_{H1',H2'}$=7.9 Hz, J$_{H2',H3'}$=5.3 Hz), 2.52 (s, 1H, OH), 2.38 (q, 24H, —CH$_2$), 0.52 (t, 36H, —CH$_3$). $^{31}$P NMR (121.5 MHz, methanol-d$_4$, H$_3$PO$_4$ as external standard) $\delta$ –8.24 (d, P$_\alpha$, J$_{P\gamma P\beta}$=21 Hz), –11.27 (d, P$_{60}$, J$_{P\alpha,P\beta}$=21 Hz), –22.43 (t, P$_{\beta, J}$=21 Hz).

5'Iodo,2'-amino,2'-deoxyuridine 5'-triphosphate

To a solution of tetrakis(triethylammonium)-2'-amino,2'-deoxyuridine 5'-triphosphate (35.2 mg, 0.02 mmoles, 0.02M) in sodium acetate (0.1M, 2 ml, pH 6.0) was added a solution of mercuric acetate (63.74 mg in 0.1M sodium acetate, 0.01M). The mixture was heated at 50° C. for 3 h. After cooling to room temperature, a solution of iodine in ethanol (25.38 mg I$_2$ in 80 $\mu$l ethanol) was added. The mixture was stirred at room temperature in the dark for 1 h. The product was purified by DEAE Sephadex-A25 (Pharmacia) chromatography (0–1M triethyl ammonium bicarbonate buffer). To remove excess buffer salt the product was repeatedly concentrated from methanol to yield 6 mg (30%) tetrakis(triethylammonium)-5-iodo,2'-amino,2'-deoxyuridine 5'-triphosphate. UV: $\lambda$max 273 nm.

EXAMPLE 6

In Vivo Stability of 2'-NH$_2$ Modified RNA Ligands of Thrombin

A study was conducted to evaluate the plasma kinetics of a thrombin ligand (38-mer) (PK-5) modified with 2'-NH$_2$ groups on the pyrimidines.

Figure 11:
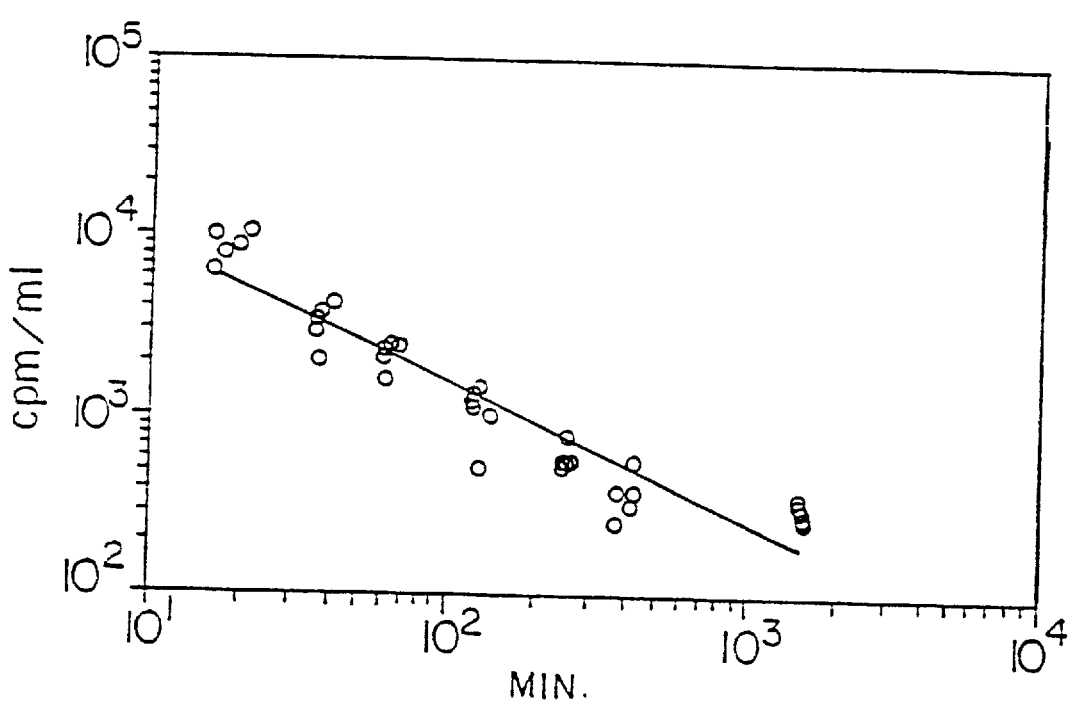
FIG. 11 shows the plasma kinetic curves obtained for each of 5 experimental rats injected with $^{32}$-P labelled RNA ligand for thrombin. Blood samples were collected at 1, 2, 4, 7, and 24 hours.

Plasma kinetic curves were obtained for five rats. Each of five male Sprague-Dawley rats was injected intravenously with 1 $\mu$Ci of $^{32}$P labelled oligonucleotide. Blood samples were collected at 15 and 30 minutes and at 1, 2, 4, 7, and 24 hours into tubes containing EDTA. Plasma was separated from the cells and phenol precipitated. 10 $\mu$l samples of the plasma were quantitated for radioactivity by scintillation counting. FIG. 11 shows the plasma kinetic curves obtained for each experimental animal.

The shape of the plasma kinetic curve was similar to that observed with a 2'-OCH$_3$ stabilized oligonucleotide of similar length which distributes rapidly into total body water and remains stable in vivo for at least 6 hours. A distribution phase half-life of 4 minutes was reported for an unstabilized, phosphodiester 20-mer oligodeoxynucleotide administered intravenously to rabbits (Goodchild et al. (1991) Antisense Res. and Dev. 1:153). No published in vivo data were found for plasma half-life of oligoribonucleotides. However, in vitro data have shown them to be even less stable than oligodeoxynucleotides in the presence of serum nucleases (Crooke (1992) Annu. Rev. Pharmacol. Toxicol. 32:329).

EXAMPLE 7

Introduction of Functional Groups

Figure 5:
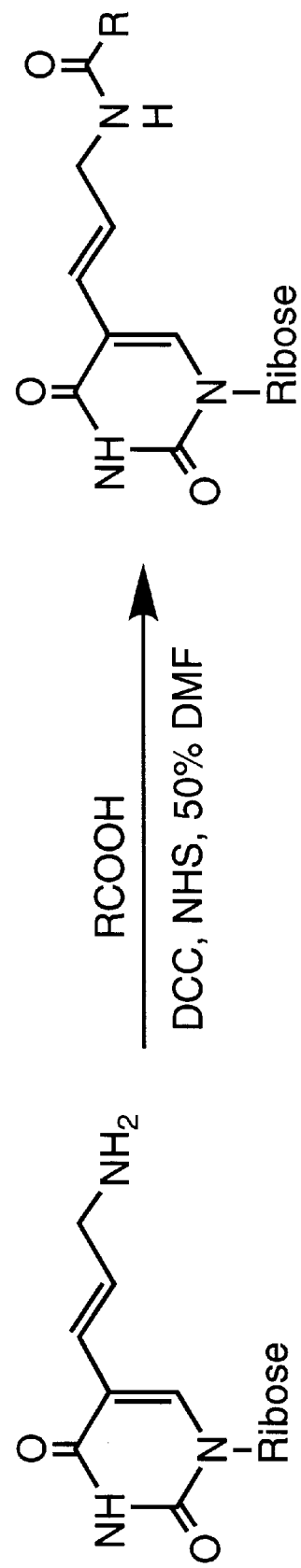
FIG. 5 shows how a variety of functional groups can be introduced into the primary amine group of 5-AA-UTP and 5-AA-dUTP by the carbodiimide/N-hydroxy succinimide coupling.
Figure 7B:
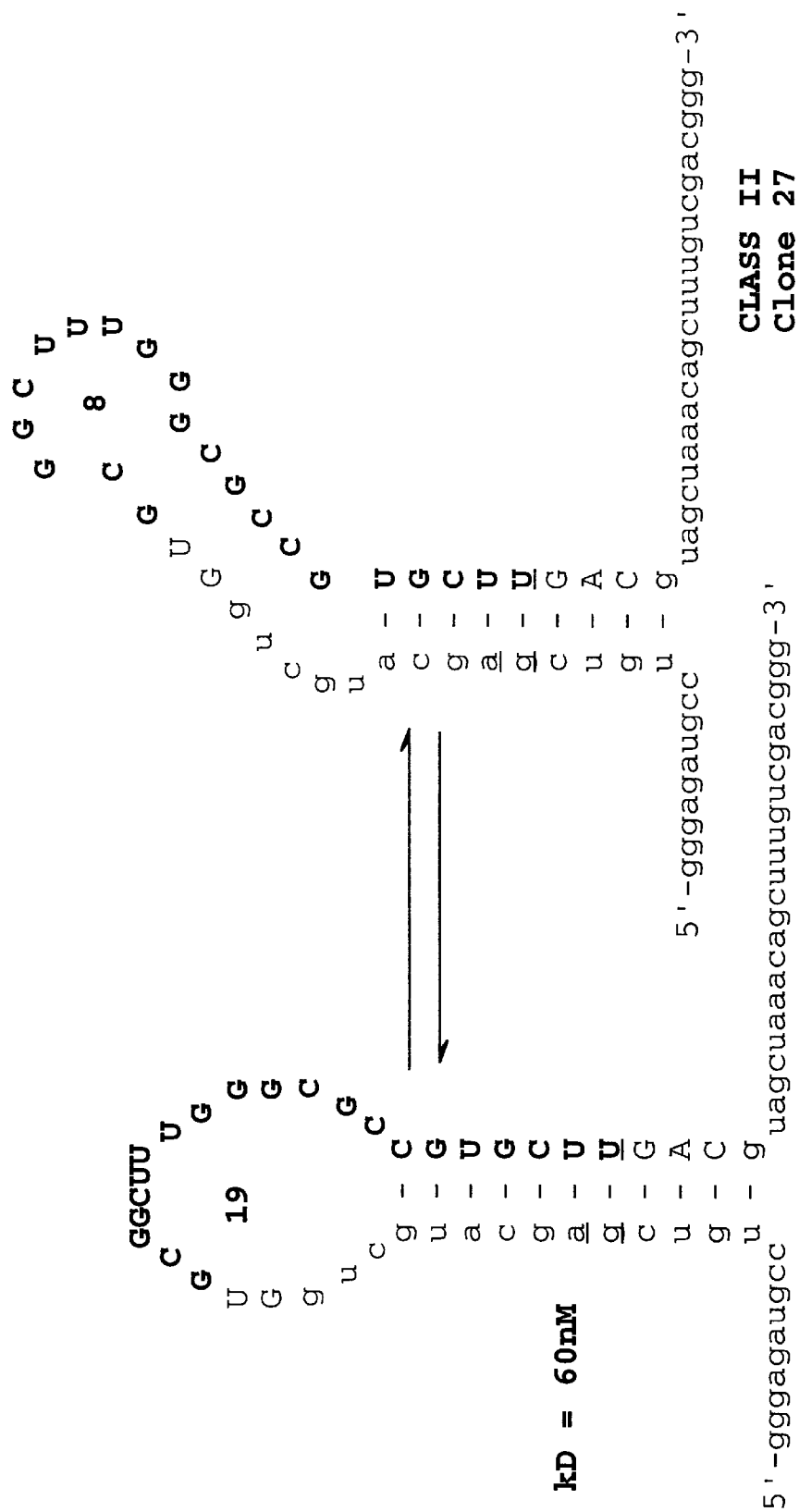

5-AA-UTP and 5-AA-dUTP contain a primary amine functionality which is useful since a wide variety of other functional groups can be readily introduced by the carbodiimide/N-hydroxysuccinimide coupling, as shown by Muhlegger et al. (1989) Nucleosides & Nucleotides 8:1161 (FIG. 5). Global physico-chemical properties of the modified oligonucleotides such as hydrophobicity or the overall charge can be modified with the addition of appropriate "side chains". Additionally, molecules that are known to bind at well-defined sites on given target molecules may be used in this context to anchor the binding of nucleic acid ligands to specific regions on the target molecule. Such moieties themselves need only modest affinities for their target molecules since the oligonucleotide framework would be evolved to provide additional binding energy. An example of this strategy is given in FIG. 5.

We claim:

1. A method for identifying nucleic acid ligands comprising a modified nucleotide to a target molecule comprising:

a) preparing a candidate mixture of single-stranded nucleic acids wherein each nucleic acid of said candidate mixture comprises a modified nucleotide;

b) contacting the candidate mixture with said target molecule;

c) partitioning the nucleic acids having an increased affinity to the target molecule relative to the candidate mixture from the remainder of the candidate mixture; and d) amplifying the increased affinity nucleic acids, in vitro, to yield a ligand-enriched mixture of nucleic acids, whereby nucleic acid ligands comprising modified nucleotides of the target molecule are identified.

2. The method of claim 1 further comprising e) repeating steps c) and d).

3. The method of claim 1 wherein said single-stranded nucleic acids are selected from the group consisting of single-stranded DNA and single-stranded RNA.

4. The method of claim 1 wherein said modified nucleotides have been chemically modified at the ribose and/or phosphate and/or base positions.

5. A nucleic acid ligand comprising a modified nucleotide to a target molecule, wherein said nucleic acid is comprised of a non-naturally occurring nucleic acid having a specific binding affinity for a target molecule, said target molecule being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by the target molecule, obtained by the process of identifying a nucleic acid ligand of a target from a candidate mixture of nucleic acids wherein each nucleic acid of said candidate mixture comprises a modified nucleotide, said process comprising:

(a) contacting the candidate mixture with said target molecule;

(b) partitioning the nucleic acids having an increased affinity to the target molecule relative to the candidate mixture from the remainder of the candidate mixture; and (c) amplifying the increased affinity nucleic acids, in vitro, to yield a ligand-enriched mixture of nucleic acids, whereby nucleic acid ligands comprising modified nucleotides of the target molecule are identified.

6. The nucleic acid ligand of claim 5 wherein said nucleic acid is selected from the group consisting of single-stranded RNA, double-stranded RNA, single-stranded DNA and double-stranded DNA.

7. The nucleic acid ligand of claim 5 wherein said nucleic acid comprises one or more or a combination of nucleotides which have been chemically modified at the ribose and/or phosphate and/or base positions.

8. The nucleic acid ligand of claim 7 wherein said nucleotide is modified at the 2'- or 5- position.

9. The nucleic acid ligand of claim 8 wherein said 2'-position modification to said nucleotide is a 2'-amino modification.

10. The nucleic acid ligand of claim 8 wherein said 2'-position modification to said nucleotide is a 2'-fluoro modification.

11. The nucleic acid ligand of claim 8 wherein said 5-position modified nucleotide is selected from the group consisting of 5-(3-aminoallyl)uridine triphosphate (5-AA-UTP), 5-fluorescein-12-uridine triphosphate (5-F-12-UTP), 5-digoxygenin-11-uridine triphosphate (5-Dig-11-UTP), and 5-bromouridine triphosphate (5-Br-UTP).

12. The nucleic acid ligand of claim 8 wherein said modified nucleotide is selected from the group consisting of a 2'-position modified pyrimidine and a 5-position modified pyrimidine.

13. The nucleic acid ligand of claim 9 wherein said modified nucleotide is selected from the group consisting of a 2'-amino pyrimidine and a 2'-amino purine.

14. The nucleic acid ligand of claim 9 wherein said modified nucleotide is selected from the group consisting of a 2'-fluoro pyrimidine and a 2'-fluoro purine.

15. A nucleic acid ligand comprising a modified nucleotide to a target molecule, wherein said nucleic acid is comprised of a non-naturally occurring nucleic acid having a specific binding affinity for a target molecule, such target molecule being a three dimensional chemical structure other than a polynucleotide that binds to said nucleic acid ligand through a mechanism which predominantly depends on Watson/Crick base pairing or triple helix binding, wherein said nucleic acid ligand is not a nucleic acid having the known physiological function of being bound by the target molecule.

16. The nucleic acid ligand of claim 15 wherein said nucleic acid is selected from the group consisting of single-stranded RNA, double-stranded RNA, single-stranded DNA and double-stranded DNA.

17. The nucleic acid ligand of claim 15 wherein said nucleic acid comprises one or more or a combination of nucleotides which have been chemically modified at the ribose and/or phosphate and/or base positions.

18. The nucleic acid ligand of claim 17 wherein said nucleotide is modified at the 2'- or 5- position.

19. The nucleic acid ligand of claim 18 wherein said 2'-position modification to said nucleotide is a 2'-amino modification.

20. The nucleic acid ligand of claim 18 wherein said 2'-position modification to said nucleotide is a 2'-fluoro modification.

21. The nucleic acid ligand of claim 18 wherein said 5-position modified nucleotide is selected from the group consisting of 5-(3-aminoallyl)uridine triphosphate (5-AA-UTP), 5-fluorescein-12-uridine triphosphate (5-F-12-UTP), 5-digoxygenin- 11-uridine triphosphate (5-Dig-11-UTP), and 5-bromouridine triphosphate (5-Br-UTP).

22. The nucleic acid ligand of claim 18 wherein said modified nucleotide is selected from the group consisting of a 2'-position modified pyrimidine and a 5-position modified pyrimidine.

23. The nucleic acid ligand of claim 19 wherein said modified nucleotide is selected from the group consisting of a 2'-amino pyrimidine and a 2'-amino purine.

24. The nucleic acid ligand of claim 19 wherein said modified nucleotide is selected from the group consisting of a 2'-fluoro pyrimidine and a 2'-fluoro purine.

* * * * *